(12) United States Patent
Taicher

(10) Patent No.: US 10,197,564 B2
(45) Date of Patent: Feb. 5, 2019

(54) NUCLEAR MAGNETIC RESONANCE APPARATUS AND METHODS

(71) Applicant: Gersh Z. Taicher, Singapore (SG)

(72) Inventor: Gersh Z. Taicher, Singapore (SG)

( * ) Notice: Subject to any disclaimer, the term of this patent is extended or adjusted under 35 U.S.C. 154(b) by 1230 days.

(21) Appl. No.: 14/340,591

(22) Filed: Jul. 25, 2014

(65) Prior Publication Data

US 2016/0025826 A1 Jan. 28, 2016

(51) Int. Cl.
| | |
|---|---|
| *G01N 33/543* | (2006.01) |
| *G01R 33/46* | (2006.01) |
| *G01R 33/34* | (2006.01) |
| *G01R 33/30* | (2006.01) |
| *G01R 33/383* | (2006.01) |
| *G01N 24/08* | (2006.01) |
| *G01R 33/38* | (2006.01) |
| *G01R 33/44* | (2006.01) |

(52) U.S. Cl.
CPC ....... *G01N 33/54366* (2013.01); *G01R 33/30* (2013.01); *G01N 24/08* (2013.01); *G01R 33/302* (2013.01); *G01R 33/34053* (2013.01); *G01R 33/34092* (2013.01); *G01R 33/383* (2013.01); *G01R 33/3806* (2013.01); *G01R 33/448* (2013.01); *G01R 33/46* (2013.01)

(58) Field of Classification Search
CPC .............. G01R 33/448; G01R 33/5615; G01R 33/4641; G01R 33/4816; G01R 33/50; G01R 33/5602; G01R 33/38; G01R 31/10; G01R 33/3607; G01R 31/318519
See application file for complete search history.

(56) References Cited

U.S. PATENT DOCUMENTS

| | | | |
|---|---|---|---|
| 4,710,713 A | 12/1987 | Taicher et al. | |
| 4,717,877 A | 1/1988 | Taicher et al. | |
| 4,717,878 A | 1/1988 | Taicher et al. | |
| 4,933,638 A | 6/1990 | Kleingerg et al. | |
| 5,055,787 A | 10/1991 | Kleinberg et al. | |
| 5,698,979 A | 12/1997 | Taicher et al. | |
| 6,346,813 B1 | 2/2002 | Kleinberg | |
| 6,653,832 B2 * | 11/2003 | Wind | G01R 33/307 |
| | | | 324/307 |
| 6,670,811 B2 * | 12/2003 | Wind | G01R 33/307 |
| | | | 324/307 |
| 6,836,115 B2 * | 12/2004 | Wind | G01R 33/54 |
| | | | 324/307 |
| 7,343,192 B2 * | 3/2008 | Reiderman | A61B 5/055 |
| | | | 324/309 |
| 7,355,402 B1 | 4/2008 | Taicher et al. | |
| 7,366,559 B2 * | 4/2008 | Taicher | G01R 33/44 |
| | | | 324/307 |

(Continued)

FOREIGN PATENT DOCUMENTS

WO 2012118442 A1 9/2012

*Primary Examiner* — Dixomara Vargas
(74) *Attorney, Agent, or Firm* — Richard A. Fagin

(57) ABSTRACT

A nuclear magnetic resonance (NMR) apparatus includes at least one magnet arranged to induce a static magnetic field in a sample chamber. The static magnetic field has a known amplitude distribution. At least one radio frequency antenna is configured to induce a radio frequency magnetic field in the sample chamber at a predetermined frequency and a predetermines bandwidth. The static magnetic field amplitude at a sample chamber boundary has substantially at most two values.

15 Claims, 21 Drawing Sheets

(56) References Cited

U.S. PATENT DOCUMENTS

| | | | |
|---|---|---|---|
| 7,366,560 B2 * | 4/2008 | Taicher | A61B 5/055 324/307 |
| 7,368,909 B2 * | 5/2008 | Blanz | E21B 49/00 324/300 |
| 8,064,982 B2 * | 11/2011 | Hu | G01R 33/485 324/307 |
| 8,334,693 B2 | 12/2012 | Lee | |
| 8,519,708 B2 | 8/2013 | Prado et al. | |
| 8,704,517 B2 | 4/2014 | Lee | |
| 2016/0025825 A1 * | 1/2016 | Taicher | G01R 33/383 324/309 |
| 2016/0025827 A1 * | 1/2016 | Taicher | G01R 33/465 436/501 |

* cited by examiner

NUCLEAR MAGNETIC RESONANCE APPARATUS AND METHODS

CROSS-REFERENCE TO RELATED APPLICATIONS

Not Applicable.

STATEMENT REGARDING FEDERALLY SPONSORED RESEARCH OR DEVELOPMENT

Not applicable.

BACKGROUND

This disclosure is related to the field of nuclear magnetic resonance (NMR) apparatus and methods. More specifically, the disclosure is related to NMR apparatus configured for measurement of surface and bulk NMR properties of very small liquid samples, for example, to detect the presence of certain substances in the very small liquid sample.

More particularly, the disclosure relates to methods and apparatus for using NMR for differentiation of fluid properties in the bulk of a fluid sample and in a layer of the fluid that interacts with a surface. In one aspect, methods and apparatus according to the disclosure relate to using NMR for rapid quantitative determination of cell conjugation. In another example aspect, methods and apparatus according to the disclosure relate to using NMR in toxicology as a rapid presumptive screen for certain classes of drugs. In yet another aspect, methods and apparatus according to the disclosure relate to using NMR in disease diagnosis to evaluate either the presence of an antigen or the presence of an antibody in a serum or other fluid sample.

The description herein and its background will be approached in the context of detecting the presence of an antigen in a sample. There is no intention to limit the generality of the present disclosure to the field of detecting the presence of an antigen in a sample.

Enzyme-linked immunosorbent assay (ELISA) is a test that uses antibodies and color change to identify a substance. In direct-ELISA a labeled primary antibody reacts directly with an antigen. Indirect-ELISA uses an unlabeled primary antibody in conjunction with a labeled secondary antibody. Since the labeled secondary antibody is directed against all antibodies of a given species, Indirect ELISA can be used with a wide variety of primary antibodies.

Antibody-sandwich ELISAs are a very useful type of immunosorbent assay for detecting antigens because they are frequently between 2 and 5 times more sensitive than those in which the antigen is directly bound to a solid phase. To detect the antigen, the wells of sample size microtiter plates (2 to 3 cubic centimeters) are coated with a specific (capture) antibody followed by incubation with test solutions containing an antigen. Unbound antigen is washed out and an antigen-specific antibody is conjugated to an enzyme (i.e., a developing reagent is added), followed by another incubation. Enzyme labeled antibody can be produced in a laboratory animal that produces passively adsorbed antibody, or from a different species immunized with the same antigen that is captured. Unbound conjugate is washed out and a substrate is added. After another incubation, the degree of substrate hydrolysis is measured. The amount of substrate hydrolyzed is proportional to the amount of antigen in the test solution.

NMR signals as used methods according to the present disclosure arise from the nuclei of hydrogen atoms in water molecules. Once generated, the magnitude of the NMR signal decays according to transverse (T2) and longitudinal (T1) relaxation properties of the water-containing material being analyzed. Spin-spin (T2) relaxation occurs when a given ensemble of oscillating hydrogen nuclear axis spins lose coherence. Loss of spin coherence is caused by macroscopic and microscopic fluctuations in the static magnetic field experienced by a freely diffusing nuclear axis spin. The former is commonly referred to as T2* relaxation and the latter as T2 relaxation. T2 relaxation contains information about the microscopic environment experienced by the hydrogen nuclei in the water-containing material. T2 relaxation can be measured independently from T2* by means of a specialized series of RF pulses and delays, called a CPMG (Can Purcell Meiboom Gill) pulse sequence. A CPMG pulse sequence removes the effects of macroscopic static magnetic field inhomogeneities to specifically measure the contribution from the microscopic environment, by creating a series of spin echoes. The relaxation time is significantly shorter for a molecule proximate a sample chamber surface or wall area, as compared to a molecule in the bulk volume. This is an effect of paramagnetic centers at a wall surface that causes the relaxation time to be faster.

T2 measurements can be carried out in real time during an analyte-induced response. T2 changes as a function of measurement time and the rate of T2 change can be correlated to a quantitative amount of analyte. The measured T2 values can be influenced by several assay, instrument, measurement, and processing parameters. For example, the measured T2 values may depend on the static magnetic field strength and homogeneity and the total spin echo measurement time. Additional parameters and variables may include valency and size of the analyte, and sample temperature. As a result, T2 values may increase or decrease with time.

Sample mixing and loading, as well as T2 measurements, can be completed in tens of seconds, making sample incubation the rate-limiting step for magnetic resonance switching (MRSw) measurements. Incubation times may be as long as several hundreds of minutes. NMR measurement of spin-lattice (T1) relaxation and diffusion takes longer than T2 measurement, but can provide valuable information related to fluid-surface interaction.

BRIEF DESCRIPTION OF THE DRAWINGS

FIG. 4 shown how a sample can be constrained into a very narrow cylindrical annulus (about 0.1 mm radially).

FIG. 5 also illustrates how a sample can be constrained into a very narrow cylindrical annulus (about 0.1 mm radially). The static magnetic field is perpendicular to the axis and an RF magnetic field is parallel to the axis.

DETAILED DESCRIPTION

Figure 1:
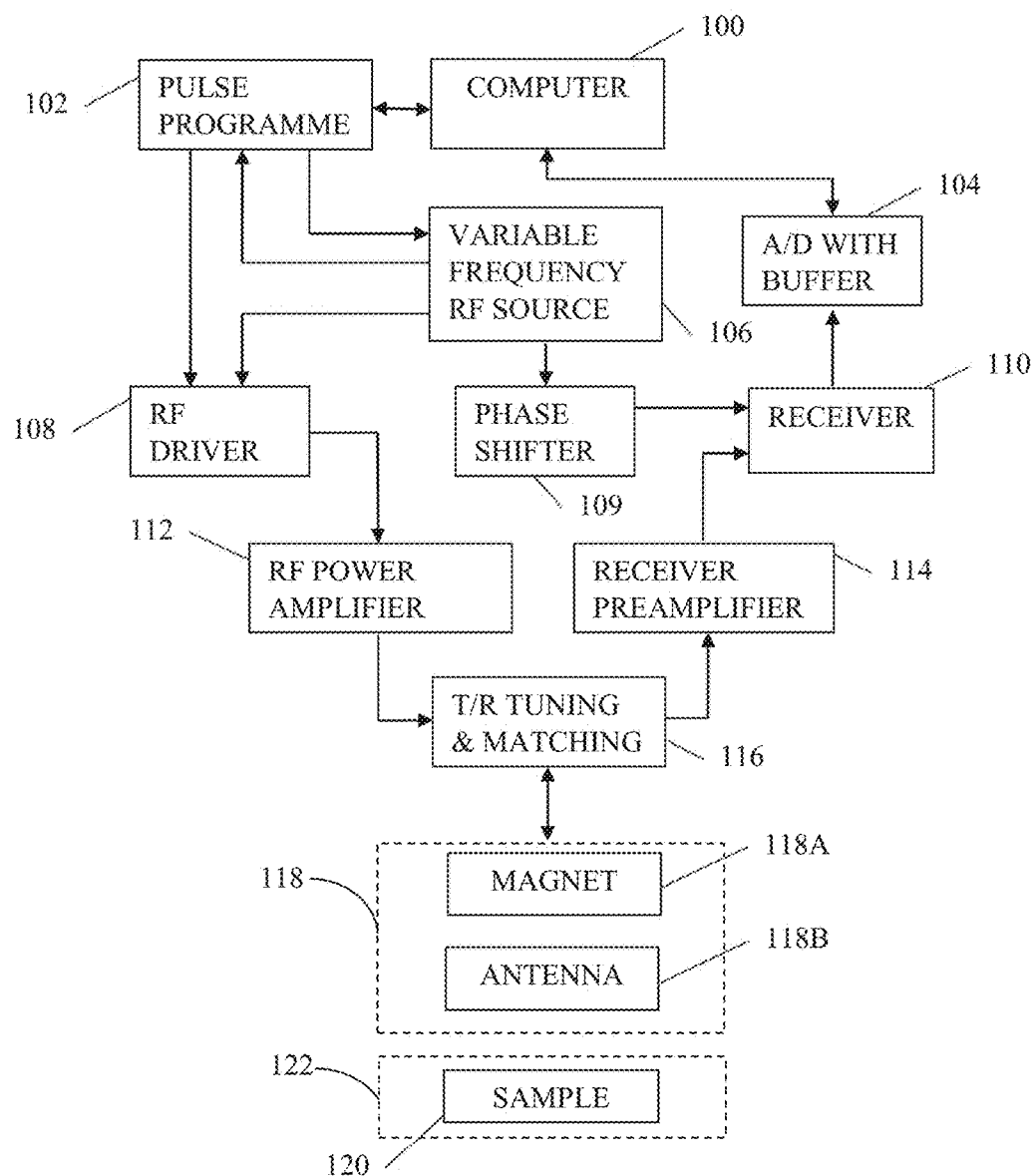
FIG. 1 is a functional block diagram of an example nuclear magnetic resonance (NMR) sensing apparatus.

FIG. 1 shows a functional block diagram of a nuclear magnetic resonance (NMR) apparatus that may be used in some embodiments. A transmitter/receiver (T/R) tuning and matching circuit 116 may be directly, or as will be explained with reference to FIG. 11, electromagnetically coupled to a sensor 118. The T/R tuning and matching circuit 116 typically includes a series of resonance capacitors (not shown separately), a transmitter/receiver switch (not shown separately) and both "to-transmitter" and "to-receiver" matching circuitry. The T/R tuning and matching circuit 116 may be coupled both to a radio frequency (RF) power amplifier 112 and to a receiver preamplifier 114. The locations of the T/R tuning and matching circuit 116, the RF power amplifier 112 and the receiver preamplifier 114 are not to be construed as a limitation on the scope of the present disclosure.

Part of the control circuitry for the NMR apparatus may include a processor or computer 100, which among other functions may provide control signals to a pulse programmer 102. The processor or computer 100 may be implemented in any known manner, including, without limitation as a field programmable gate array, electrically erasable read only memory, microprocessor, application specific integrated circuit, digital signal processor or the like. The pulse programmer 102 controls the timing and operation of a variable frequency RF signal source 106. An RF driver 108 receives an input from the variable frequency RF source 106 and provides an output to the RF power amplifier 112. The RF power amplifier 112 provides a high power signal to drive a transceiver antenna 118B for generating an RF magnetic field in a sensitive volume to be further described in detail below. The RF power amplifier 112 may be directly connected (typically by a switch in the T/R tuning and matching circuit 116) to the transceiver antenna 118B during transmission of RF power pulses, or may be electromagnetically coupled as will be explained with reference to FIG. 11.

During detection of induced NMR signals, the transceiver antenna 118B and/or an additional receiver antenna (FIGS. 12, 13A and 13B) can be electrically connected to the receiver preamplifier 114 by means of the switch in the T/R tuning and matching circuit 116. The output of the RF receiver preamplifier 114 may be provided to an RF receiver 110. The RF receiver 110 also receives a phase reference input from a phase shifter 109. The phase shifter 109 receives a primary phase reference input from the variable frequency RF source 106. The RF receiver 110 may include quadrature detection. The RF receiver 110 provides an output to an A/D converter and buffer 104. In some embodiments several sensors configured as explained above, each corresponding to a different NMR region of interest may be used sequentially, each being switched on and off by the T/R tuning and matching circuit 116. One example may use a 96 well microtiter plate, a standard tool in analytical research and clinical diagnostic testing laboratories.

Various embodiments of the sensor 118, which will be set forth in more detail below, generally include at least one magnet 118A such as a permanent magnet or an electromagnet to induce a static magnetic field having well known amplitude and polarization direction distribution. The antenna 118B may be one or more wire coils, as will be further explained below, to induce an RF magnetic field having a known amplitude and polarization direction distribution and to detect NMR signals induced in a sample 120 being analyzed. The sample 120 is generally disposed within a NMR region of investigation (ROI) 122, in which the amplitude of the static magnetic field and the frequency of the RF magnetic field are selected to excite NMR phenomena within the sample 120.

In the description of various embodiments of an NMR apparatus according to the present disclosure, reference will be made to one or more magnets polarized in a particular direction. Depending on the particular arrangement of the one or more magnets, the amplitude distribution and the polarization direction distribution of the resulting static magnetic field may vary within any plane normal to what will be defined herein as a longitudinal axis of the apparatus. The length of the one or more magnets may be selected such that within a defined distance along the longitudinal axis, the amplitude distribution and the polarization distribution are substantially constant within the defined distance. In a similar manner, one or more radio frequency antennas may be configured to have a magnetic dipole moment orthogonal to the static magnetic field direction, however the antenna sensitivity along the longitudinal axis may be substantially constant within a selected distance along the longitudinal axis. Finally, a sample chamber may be disposed within the static magnetic field and within the radio frequency magnetic field and/or the detection region defined by the one or more radio frequency antennas such that the length of the sample chamber along the longitudinal axis is disposed entirely within the selected distance defined by the one or more radio frequency antennas.

Figure 2B:
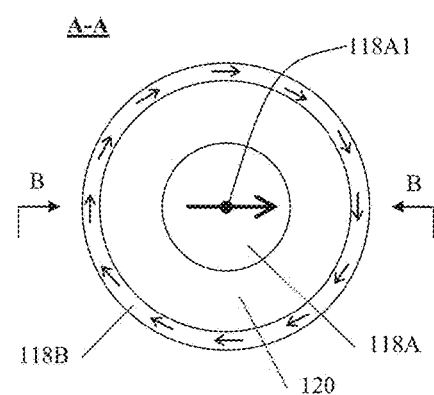
FIG. 2B is a schematic sectional illustration of the sensor as shown in FIG. 1 in a plane perpendicular to the axis indicated by the lines A-A in FIG. 2A and illustrates example arrangements of the magnet, RF coil, magnetization direction and current direction with reference to the sample being analyzed.
Figure 2A:
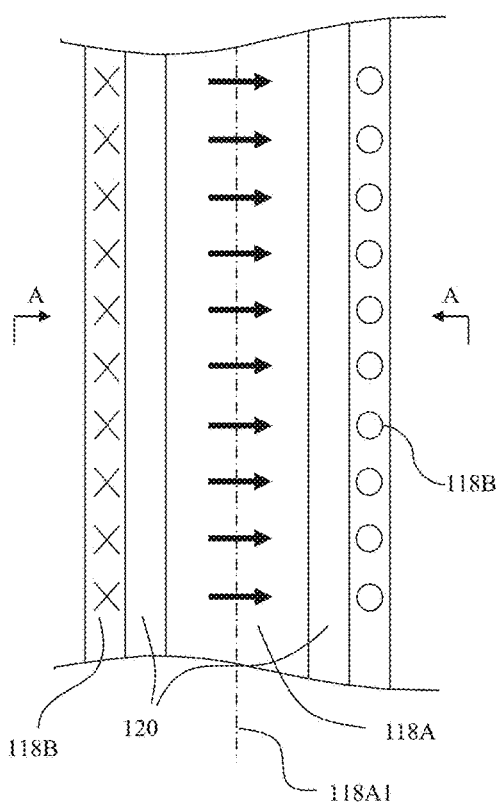
FIG. 2A is a schematic sectional illustration of a sensor as shown in FIG. 1 in a plane parallel to an axis indicated by the lines B-B in FIG. 2B, and illustrates an example arrangement of the a magnet, RF coil, magnetization direction and current direction with reference to a sample being analyzed.

FIGS. 2A and 2B show, respectively, an embodiment of the sensor 118 and the ROI 122 in vertical sectional view and top cross sectional view, respectively. The magnet 118A may be a substantially right cylindrical, transversely polarized permanent magnet. One such magnet structure is described in U.S. Pat. Nos. 4,710,713, 4,817,877 and 4,817,878 issued to Taicher et al. The magnet 118A may be polarized transversely to its cylindrical axis 118A1. The RF antenna 118B may be wound around the exterior of the magnet 118A so as to provide an annular sample volume 120 therebetween. The sample volume 120 is within the ROI 122. As will be appreciated by those skilled in the art, the amplitude distribution of the static magnetic field within the sample volume 120 is substantially constant in circles of selected radius from the axis 118A1, although the field direction is not constant. Thus, using the magnet 118A and coil 118B arrangement shown in FIGS. 2A and 2B, various annular "rings" of selected diameter between the outer surface of the magnet 118A and the inner boundary of the antenna 118B may be investigated depending on the RF frequency selected.

Figure 3A:
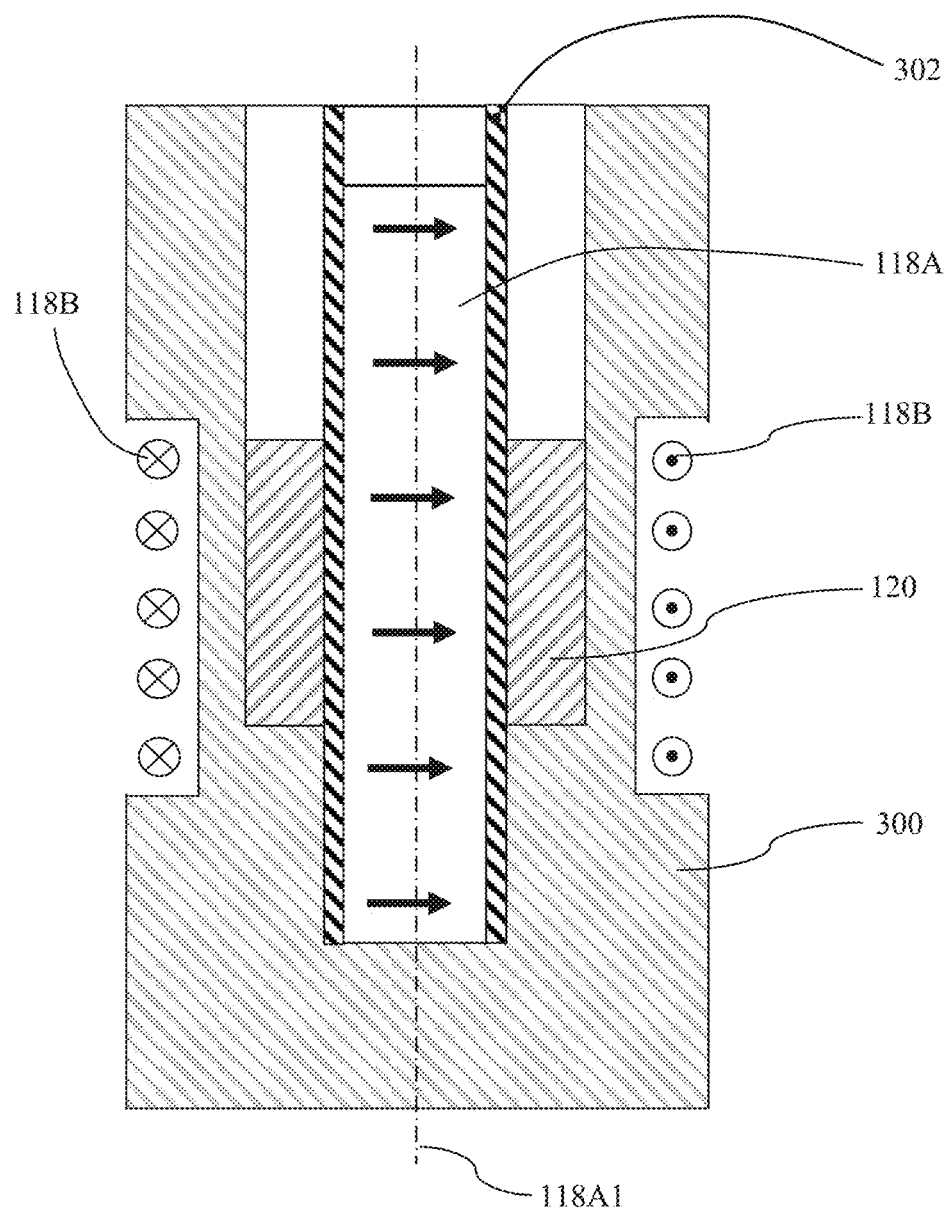
FIG. 3A is a detailed sectional illustration of the sensor as shown in FIG. 1 in a plane parallel to an axis indicated by the lines B-B in FIG. 2B and illustrates example arrangements of the magnet, RF coil, magnetization direction and the current direction with reference to the sample being analyzed.

FIG. 3A shows a vertical cross section of a sensor (118 in FIG. 1) that may be used in some embodiments. The magnet 118A may be substantially polarized transversely to its longitudinal axis 118A1 as explained with reference to FIGS. 2A and 2B and extend a length substantially longer than the longitudinal extent of the antenna 118B, which may be in the form of a solenoid coil having a common axis 118A1 with the magnet 118A. The magnet 118A may be covered on its exterior by an electrically conductive, non-magnetic RF shield made of material such as copper sheet so that no RF energy emitted by the antenna 118B extends inside the RF shield 302. The antenna 118B may be disposed on an electrically non-conductive, non-magnetic spool 300, for example, made from glass or plastic such as TEFLON brand plastic. TEFLON is a registered trademark of E.I. duPont deNemours and Company, Wilmington, Del. The spool 300 and the RF shield 302 may define an annular opening (a sample chamber) in which a sample 120 to be analyzed will be disposed. For such purposes, in some embodiments the RF shield 302 may be coated with a thin layer of material such as TEFLON brand plastic The sample 120 may generally be limited in volume such that its bottom and top longitudinal ends are well within the longitudinal ends of the antenna 118B so that a substantially uniformly directionally distributed RF magnetic field may be induced in the sample to generate NMR phenomena for measurement and analysis.

Figure 3B:
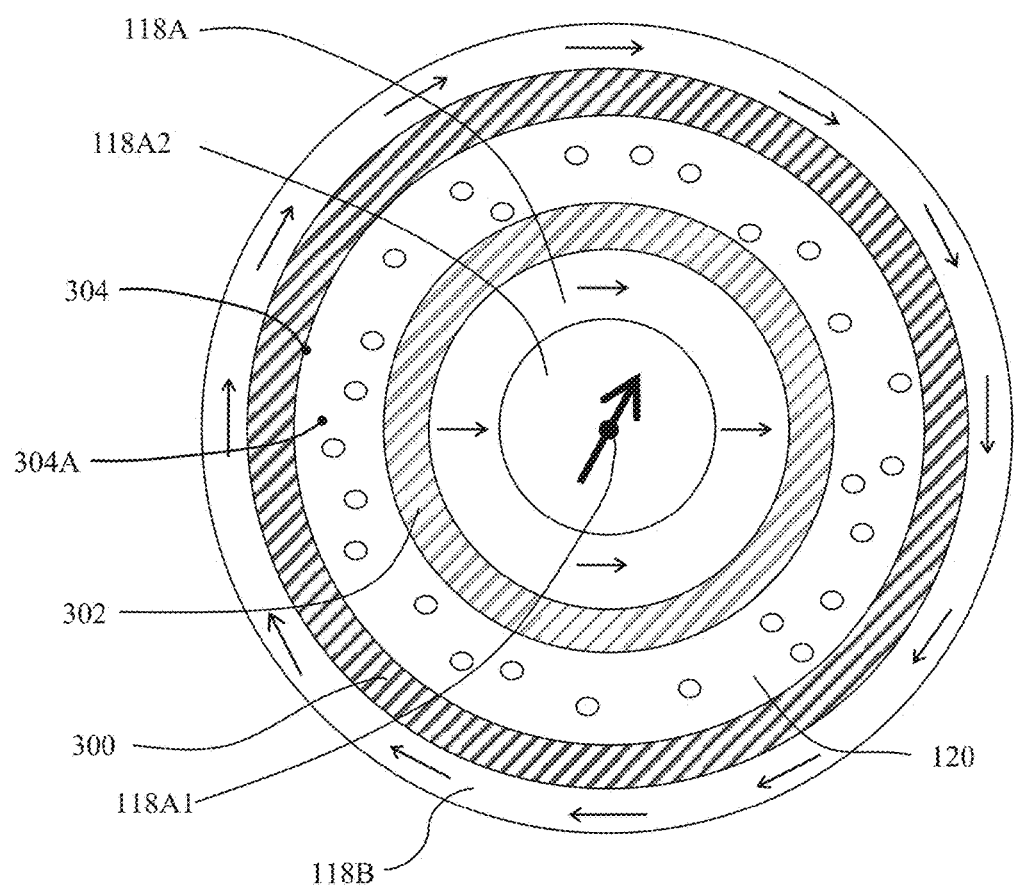
FIG. 3B is a detailed sectional illustration of the sensor shown in FIG. 1 in a plane perpendicular to an axis indicated by the lines A-A in FIG. 2A and illustrates example arrangements of the magnet, RF coil, magnetization direction and the current direction with reference to the sample being analyzed.

FIG. 3B shows a top view of the sensor embodiment shown in FIG. 3A to illustrate the relative radial positions of the various components described above. In the example embodiment shown in FIG. 3B, the magnet 118A may include an additional, substantially cylindrical magnet 118A2 in an opening in the center thereof. The additional magnet 118A2 may also be transversely polarized, and enabled to rotate within the opening in the magnet 118A. Rotation of the additional magnet 118A2 will change the amplitude of the static magnetic field within the sample 120 volume so that NMR measurements may be made within different radial zones within the sample 120 volume using the same RF frequency, or may be used to make NMR diffusion measurements as well as relaxometry measurements. In some embodiments, the magnet 118A and the additional magnet 118A2 may have substantially the same cross-sectional surface area and substantially the same magnetization material properties so that having the magnets 118A, 118A2 oriented in opposed polarization directions results in substantially zero static magnetic field amplitude external to the magnet 118A. Having zero static magnetic field amplitude may be used in some types of NMR experiments as will be explained in more detail with reference to FIGS. 14A through 14F. In some embodiments, the static magnetic field amplitude and/or the RF frequency and bandwidth may be selected such that NMR measurements are made within about 0.1 millimeters of the surfaces defined by the spool 300 or the RF shield 302. Such measurements, as will be further explained with reference to FIGS. 14A through 14F may be used in some embodiments to determine changes in surface relaxivity of the sample.

Figure 4:
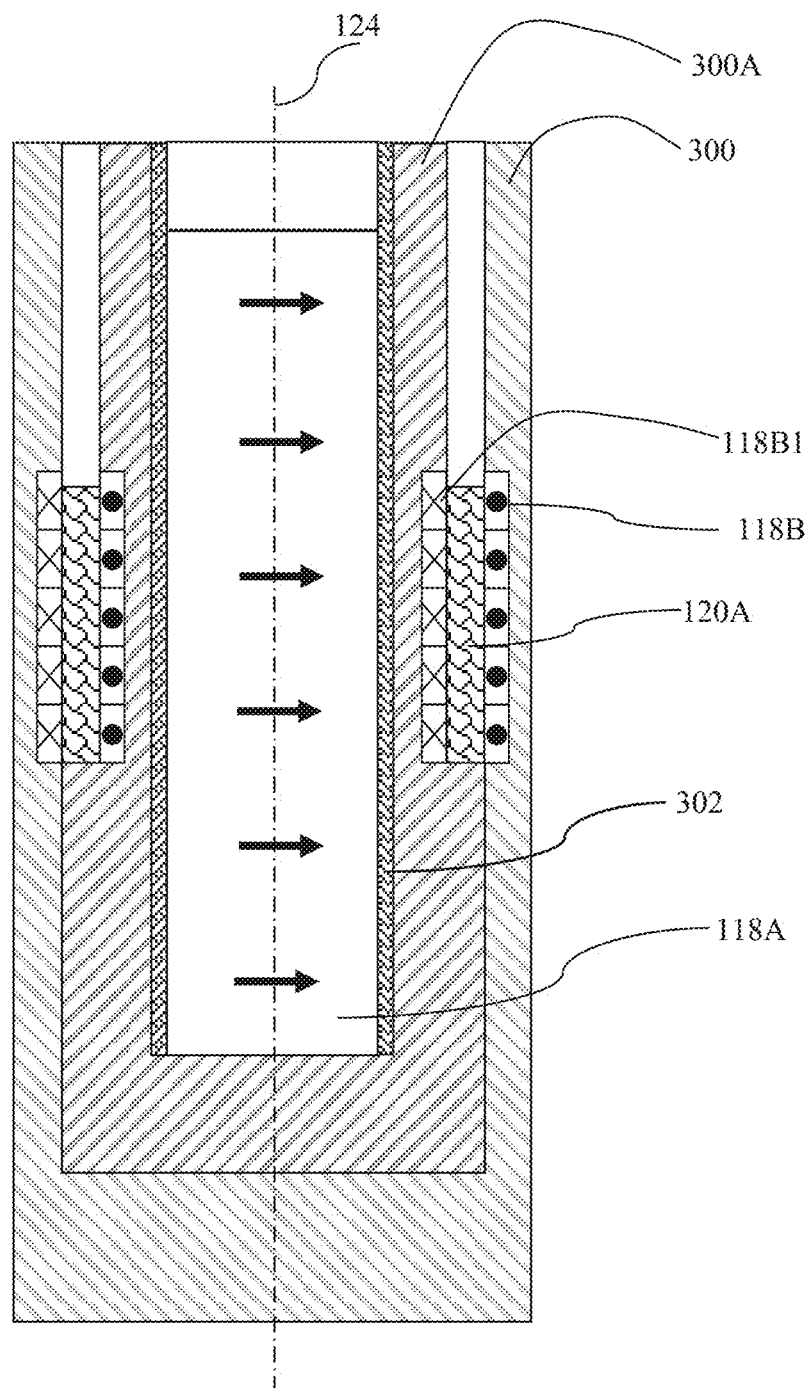
FIG. 4 is a detailed sectional illustration of the sensor shown FIG. 1 taken in a plane parallel to an axis indicated by the lines B-B in FIG. 2B and illustrates example arrangements of the magnet, RF coil, magnetization direction and current direction with reference to a sample being analyzed.
Figure 5:
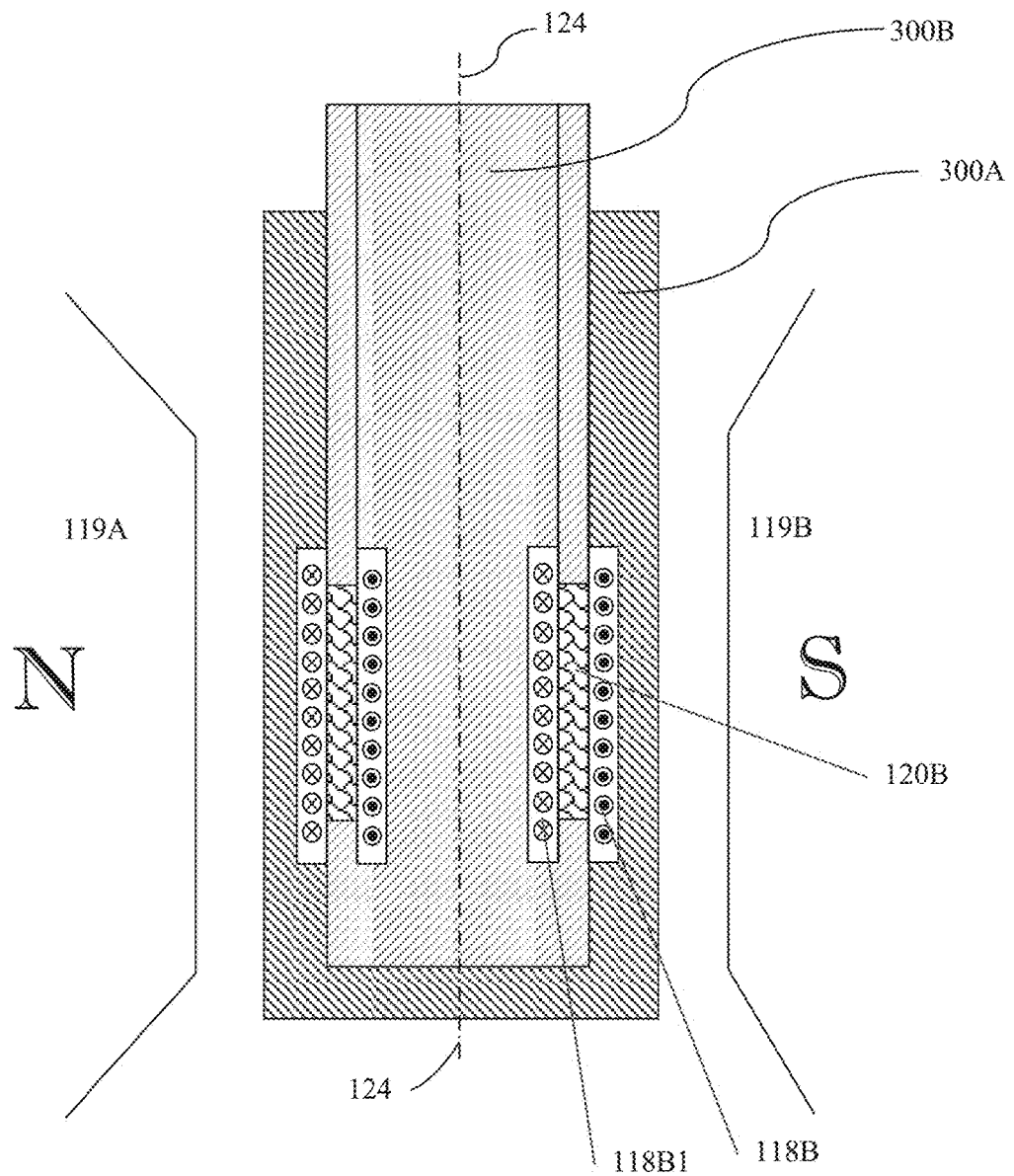
FIG. 5 is a sectional illustration of a sensor as shown in FIG. 1 in a plane parallel to an axis and illustrates example arrangements of the RF coil and a sample placed into a homogeneous external magnetic field.

FIG. 4 shows another embodiment of a sensor (118 in FIG. 1) having an inner antenna coil 118B1 at a first selected radial distance from the magnet 118A and an outer antenna coil 118B at a second selected radial distance from the magnet 118A. The sample chamber 120A may be defined within an annular space between the inner antenna coil 118B1 and the outer antenna coil 118B. A radio frequency shield 302 such as may be made from copper sheet as the embodiment of FIG. 3A may be disposed on the exterior of the magnet 118A, and the inner antenna coil 118B1 may include a separate spool 300A for winding thereon. The inner antenna coil 118B1 may be wound in a direction opposed to the winding direction of the outer antenna coil 118B so as to bound the distribution of RF energy to the space between the antenna coils 118B, 118B1. The inner and outer coils 118B, 118B1 are connected in series, have the same current amplitude and the same number of turns, but are wound in opposite directions. The embodiment shown in FIG. 4 may be used in a manner similar to the embodiment shown in FIGS. 3A and 3B, and have similar arrangements of the magnet 118A so that NMR experiments may be made for the specific purpose of detecting changes in surface relaxivity of the sample disposed in the sample chamber 120A. In some embodiments, the space between the antenna coils 118B, 118B1 may be selected such that the sample radial thickness is about 0.1 millimeters. Such radial thickness may provide that NMR measurements are made within about 0.1 millimeters of the surfaces defined by the spool 300 and the RF shield 302 at the same time. Such measurements, as will be further explained with reference to FIGS. 14A through 14F, may be used in some embodiments to determine changes in surface relaxivity of the sample. axis 124 is not explained in FIG. 4 FIG. 5 shows a similar sensor arrangement as in FIG. 4, however, the magnet shown in FIG. 4 may be substituted by two magnets 119A, 119B disposed externally to an antenna-sample and polarized such that a north pole of one magnet 119A faces the south pole of the other magnet 119B as shown. Arrangements such as shown in FIG. 5 will be described in more detail with reference to FIGS. 9A, 9B and 9C. FIG. 5 also illustrates how a sample can be constrained into a very narrow cylindrical annulus (in one embodiment about 0.1 mm radially). Such constraint may be obtained by suitable selection of the diameters of the antenna coils 118B, 118B1 and an inner spool 300B, which may be made from an electrically non-conductive, non-magnetic material such as glass or TEFLON brand plastic and a mating, outer spool 300A made from similar materials. A sample chamber 120B may be defined by a suitable recess formed into either spool 300B, 300A. The RF antenna coils 118B, 118B1 may be embedded in the material of the respective spool 300A, 300B. A static magnetic field induced by the magnets 119A, 119B is perpendicular to a longitudinal axis 124 of the antenna coils 118B, 118B1 and an RF magnetic field induced by passing RF current through the antenna coils 118B, 118B1 is parallel to the axis 124. In some embodiments, the magnets 119A, 119B may have selected dimensions and an exterior cross section of the outer RF antenna coil 118B may be selected such that the outer RF antenna coil 118B and all the components disposed within its cross-section as described above are disposed within a substantially homogeneous static magnetic field. Such a field region between the magnets 119A, 119B is illustrated in FIG. 9B in a center of the static magnetic field amplitude distribution graph shown therein. For example, in the static magnetic field distribution shown in FIG. 9B, if the size of the outer RF antenna coil 118B is limited to about 2-3 millimeters diameter, the outer RF antenna coil 118B and all the above described components disposed within its cross section will be disposed within a substantially homogeneous static magnetic field. In other embodiments, the size of the outer antenna coil 118B (and components disposed within its cross section) may be increased by correspondingly increasing the dimensions of the magnets 119A, 119B to increase the size of the region of homogeneous static magnetic field between them.

By limiting the radial dimension of the sample chamber 120B as explained above, a surface to volume ratio of the sample chamber 120B may be relatively high. By having a relatively large surface to volume ratio, a size of the sample chamber 120B may be maintained in the microliter range while generating a substantial fraction of the NMR phenomena excited within the sample chamber 120B which originates from sample materials in contact with surfaces thereof or within up to, for example, about ten molecular thicknesses of the surfaces thereof. In some embodiments, the surface to volume ratio of the sample chamber 120B may be selected such that surface-effect NMR phenomena may result in substantially all of the NMR signals detected from the sample chamber 120B. Therefore, NMR relaxometry measurements made using only a single selected static magnetic field amplitude, a single RF frequency and a single RF bandwidth may still result in NMR signals that will enable detection of any changes in the surface relaxivity or diffusion constant of a sample within the sample chamber. By limiting the radial dimension of the sample chamber 120B, diffusion may become restrictive in a sense that fluid molecules will interact with the sample surface during NMR diffusion measurements and thus change the apparent diffusion constant.

In other embodiments, a ratio of a surface of the material sample to sample chamber interface with respect to a volume of the material sample is selected such that NMR phenomena induced in the sample depend substantially entirely on material sample to sample chamber interface effects.

Example uses of such relaxivity measurements will be further explained below with reference to FIGS. 14A through 14F.

The sample chambers described with reference to FIGS. 2A, 2B, 3A, 3B, 4 and 5 may be in the form of an annular cylinder. In each of the foregoing example embodiments, the sample chamber may be disposed entirely within the "defined distance" along the longitudinal axis as explained above, wherein the static magnetic field and the RF magnetic field and/or antenna sensitivity are substantially constant along the longitudinal axis (e.g., 124 in FIGS. 5 and 118A1 in FIG. 3A). also 124 in FIG. 4?

Figure 6:
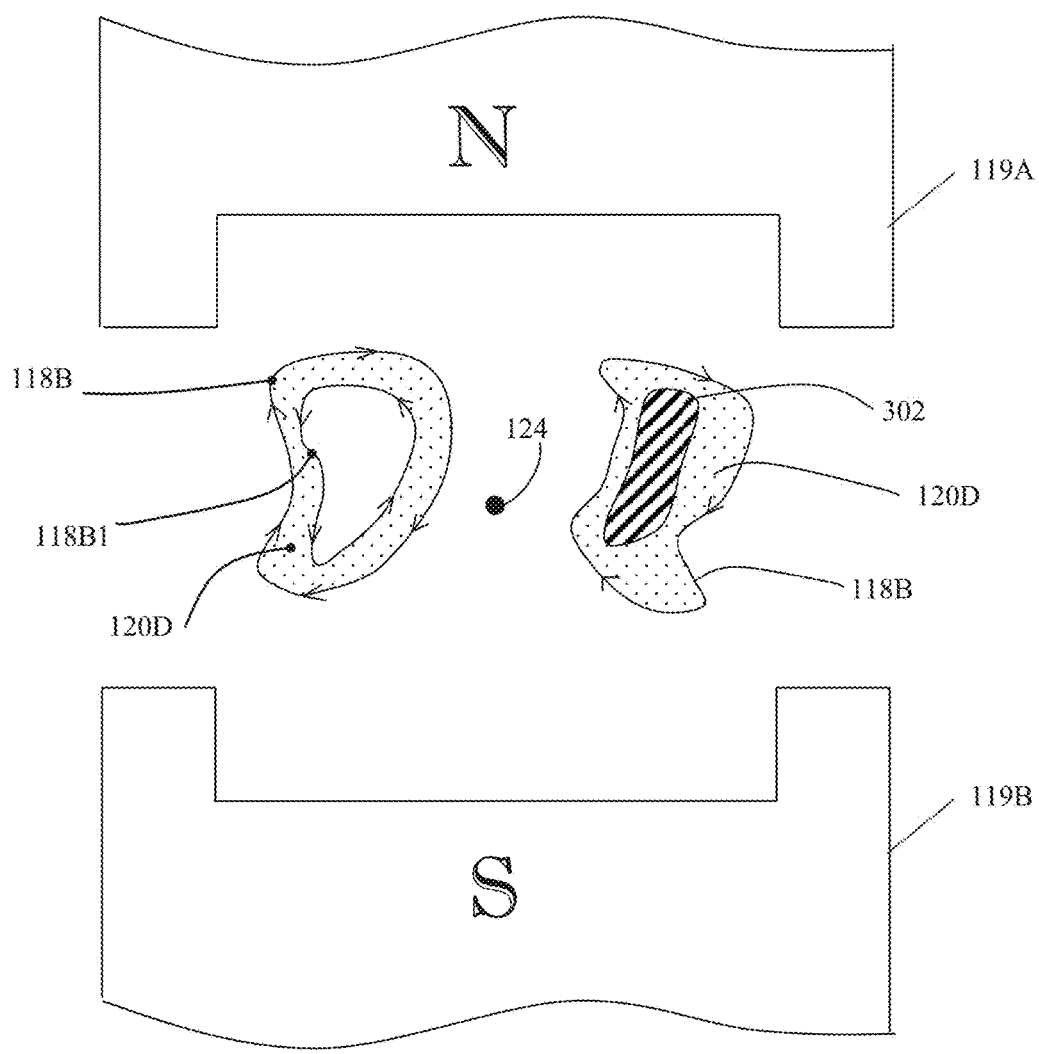
FIG. 6 is a sectional illustration of two separate sensors (one with copper shielding as in FIG. 3A and FIG. 3B; the other with a coil having opposite winding direction as in FIG. 5 and further explained with reference to FIG. 7) in a plane perpendicular to an axis and illustrates example arrangements of the RF coil and sample placed in a homogeneous (having equal amplitude, but not necessary unidirectional) external static magnetic field. The static magnetic field is perpendicular to the axis and the RF magnetic field is parallel to the axis.

FIG. 6 is a sectional illustration of two separate NMR sensors (one with RF shielding 302 as in FIG. 3A and FIG. 3B; the other with an RF antenna coil 118B1 having opposite winding direction as in FIG. 5 and further explained with reference to FIG. 7) in a plane perpendicular to an axis 124. FIG. 6 illustrates example arrangements of the RF coil 118B and sample chamber 120D placed in a homogeneous (having equal amplitude, but not necessary unidirectional) externally applied static magnetic field from two magnets 119A 119B polarized as shown. The static magnetic field is perpendicular to the axis 124 and the RF magnetic field induced by the RF antenna coils(s) 118B (and if used 118B1) is parallel to the axis 124. As explained with reference to FIG. 5, the outer RF antenna coil 118B or the RF shielding 302, whichever forms the outer boundary of a sample chamber 120D, may have arbitrary cross-sectional shape provided that the element bounding the outside of the sample chamber 120D is disposed within a region of substantially homogeneous static magnetic field. Magnet arrangements and sizes of the outer sample chamber 120D boundary to obtain such static magnetic field distribution are explained above with reference to FIG. 5.

Figure 7:
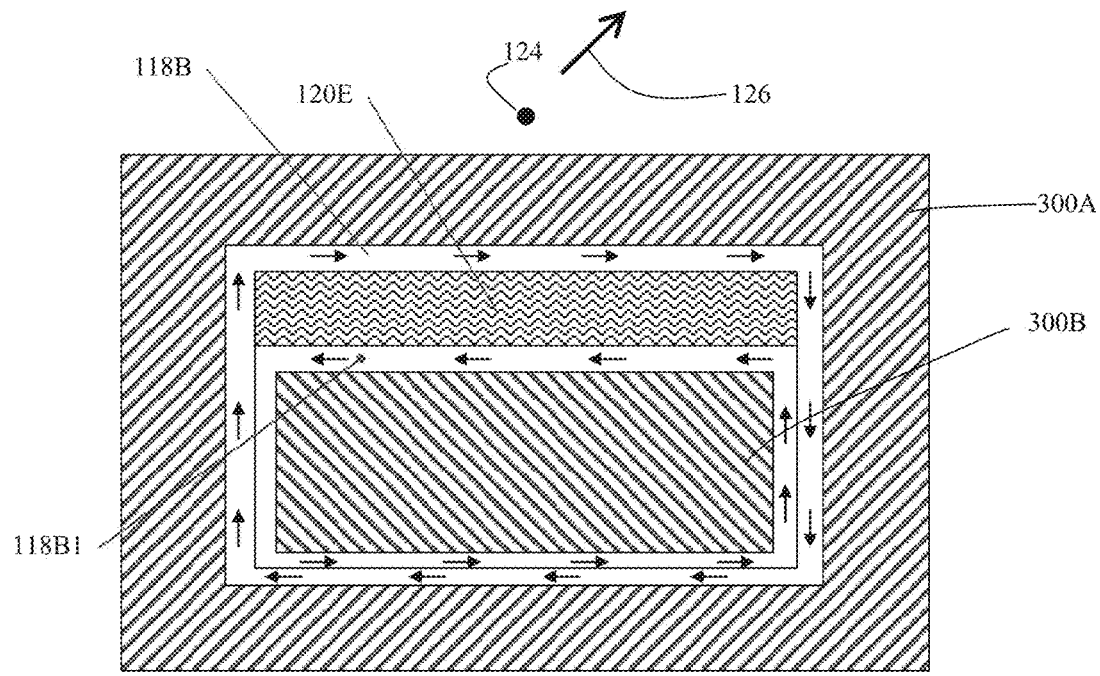
FIG. 7 is a sectional illustration of a sensor (especially useful to measure very thin samples such a blood smear over a surface) in a plane perpendicular to an axis and illustrates example arrangements of the RF coil and a sample placed into a homogeneous external static magnetic field. The static magnetic field is perpendicular to the axis and RF magnetic field is parallel to the axis. The sample in FIG. 7 is placed over a copper-coated block (or any other block having highly electrically conductive, non-magnetic surface). Alternatively, the block has a coil winding over its surface as shown in FIG. 6.

FIG. 7 is a sectional illustration of another embodiment of the sensor which may be especially useful for measuring very thin samples such a blood smear over a surface, such as a surface of a test cell (not shown separately) sized to fit substantially exactly between the inner and outer coils (118B, 118B1 in FIG. 4) in a plane perpendicular to an axis 124. FIG. 7 illustrates example arrangements of the RF antenna coil 118B disposed on the interior of an electrically non-conductive, non-magnetic holder or spool 300A and a sample chamber 120E therein placed into a homogeneous, externally imparted static magnetic field. The static magnetic field has substantially equal amplitude within the sample chamber 120E and a polarization direction 126 perpendicular to the axis 124 and the RF magnetic field emitted by the antenna coil 118B is parallel to the axis 124. The sample chamber 120E in FIG. 7 may be bounded by a copper-coated block 300B or any other block having highly electrically conductive, non-magnetic surface. In some embodiments, the block 300B may not be electrically conductive or covered with such material and may have a second antenna coil 118B1 wound over its surface and connected in opposed direction as the electrical connection of the antenna coil 118B. The static magnetic field direction 126 is substantially perpendicular to the axis 124 and in a direction indicated by the arrow. Arrangements of the sensor and the magnets so that the sample chamber 120E is disposed within a substantially equal amplitude static magnetic field are explained above with reference to FIG. 5.

Figure 8:
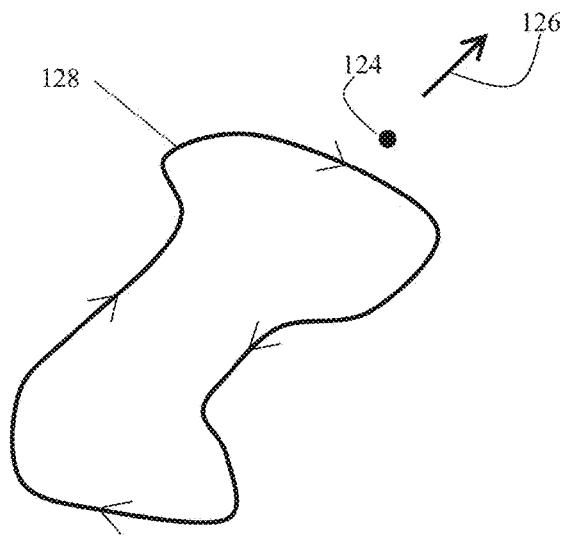
FIG. 8 is a sectional illustration of a sensor (especially useful to measure large samples that can be placed in a cylindrical test tube having a cross-section as indicated in the figure) in a plane perpendicular to an axis and illustrates an example arrangement of the RF coil and a sample placed into a homogeneous external static magnetic field. The static magnetic field is perpendicular to the axis and the RF magnetic field is parallel to the axis.

FIG. 8 is a sectional illustration of a sensor (especially useful to measure large samples that can be placed in a cylindrical test-tube having a cross-section as indicated in the figure) in a plane perpendicular to the axis 124 and illustrates an example arrangement of the RF antenna coil 128 and a sample placed into a homogeneous (in a sense of equal amplitude, not necessarily along the same polarization direction) externally imparted static magnetic field. The static magnetic field has a direction 126 perpendicular to the axis 124 and the RF magnetic field induced by passing RF current through the RF antenna coil 128 is parallel to the axis 124. The various shapes of the antenna coils, copper shielding, spools, holders and related components have a common attribute that will be explained in more detail with reference to FIGS. 9A through 9C: namely that the shape of the antenna coil 118B, a second antenna coil 118B1 if used, or RF shield 302 if used may be in a shape corresponding to contours of equal static magnetic field amplitude.

Figure 9A:
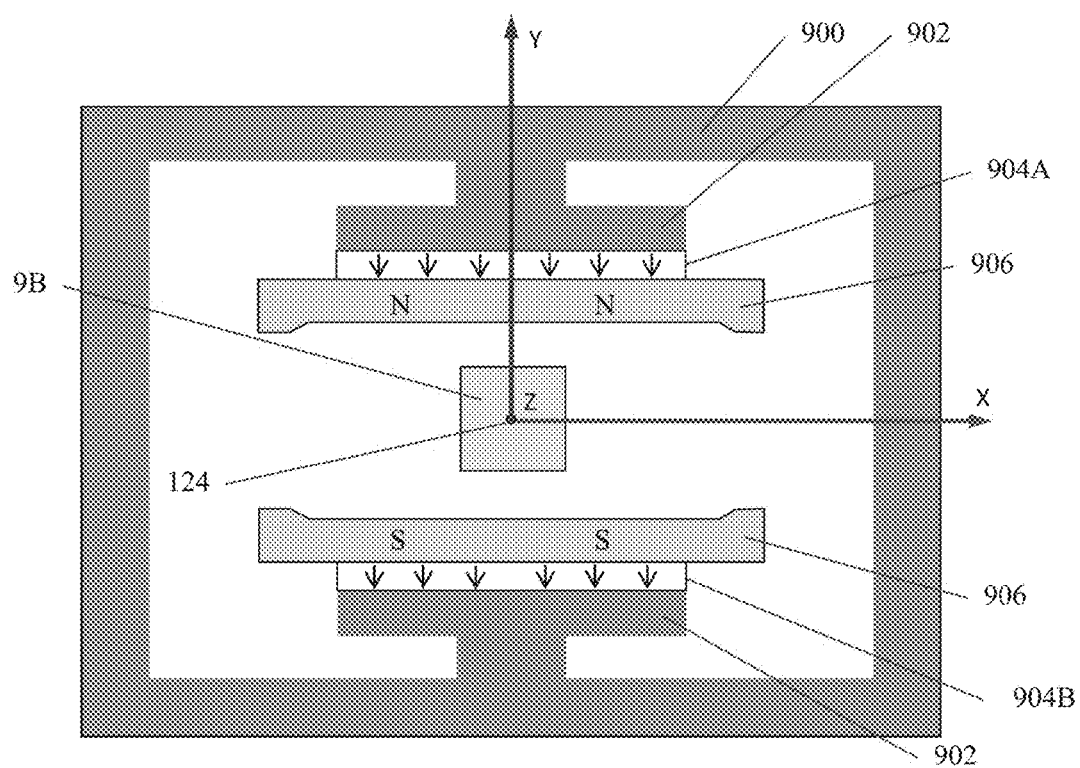
FIG. 9A is a sectional illustration of an example configuration of a permanent magnet generating a "homogeneous" magnetic field perpendicular to an axis.
Figure 9B:
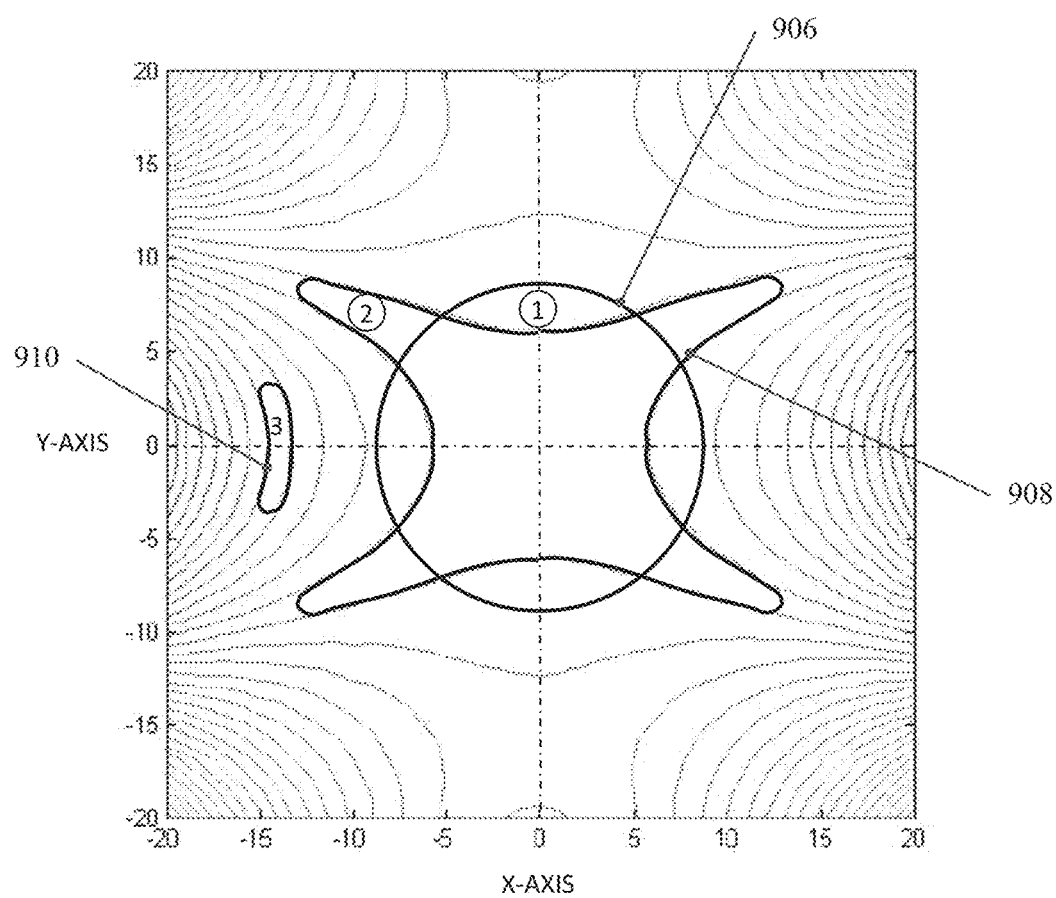
FIG. 9B is a sectional illustration of the "homogeneous" static magnetic field of the arrangement of FIG. 9A in the square shown in FIG. 9A. The field is perpendicular to an axis. Contours of equal static magnetic field amplitude are shown. Prior art test-tube having a circular cross-section is shown as "1". A second test-tube having a cross-section is shown as "2". This cross-section has twice better homogeneity as compared to "1" and roughly the same volume. A third test-tube having a cross-section is shown as "3". This cross-section has the same homogeneity as compared to "2", a smaller volume, which has no impact on S/N provides an RF coil is designed in a manner similar to one in FIG. 8. However, the "3" cross-section has a substantially uniform and homogeneous static magnetic field gradient useful for diffusion measurements.

FIG. 9A shows a cross section perpendicular to a longitudinal axis of an example of a sensor magnet chamber that induces a pseudo-homogeneous static magnetic field perpendicular to the longitudinal axis 124. A flux closure 900 may be made from steel or other soft magnetic material. The flux closure 900 may include opposed, inward facing mounting pads 902 for respective permanent magnets 904A, 904B. The magnets 904A, 904B may be polarized as shown in FIG. 9A wherein opposed poles of the magnets face each other. Each magnet 904A, 904B may be bounded on the other side thereof by a pole piece 906 shaped approximately as shown and made from steel or other soft magnetic material having high magnetic permeability. 9B indicates a central region shown in more detail in FIG. 9B in which a magnetic field amplitude distribution will be described. The X and Y axes that will be shown in FIG. 9B are indicated with reference to the flux closure 900. One contour defines a surface of a sample chamber having a maximum filed amplitude; the other contours define a surface of a sample chamber having a minimum static magnetic field amplitudes as seen on FIG. 9B in oval shaped number 3 as element 910 and FIG. 9C in oval shapes 3-6 as elements 910, 911, 912 and 913.

FIG. 9B shows the area indicated at 9B in FIG. 9A in more detail. The contour lines are lines of equal static magnetic field amplitude with respect to distance along the X and Y axes from the center axis (124 in FIG. 9A). A conventional, cylindrically shaped test chamber, such as a test tube, is indicated by contour 906. A test chamber having a contour such as shown at 908 may be expected to have twice the homogeneity of static magnetic field amplitude as the test tube having a shape of contour 906. Another contour, shown at 910, has surfaces along two contours of different but constant static magnetic field amplitude. The static magnetic field in within the contour at 910 has a substantially homogeneous gradient perpendicular to the constant amplitude contour lines.

Figure 9C:
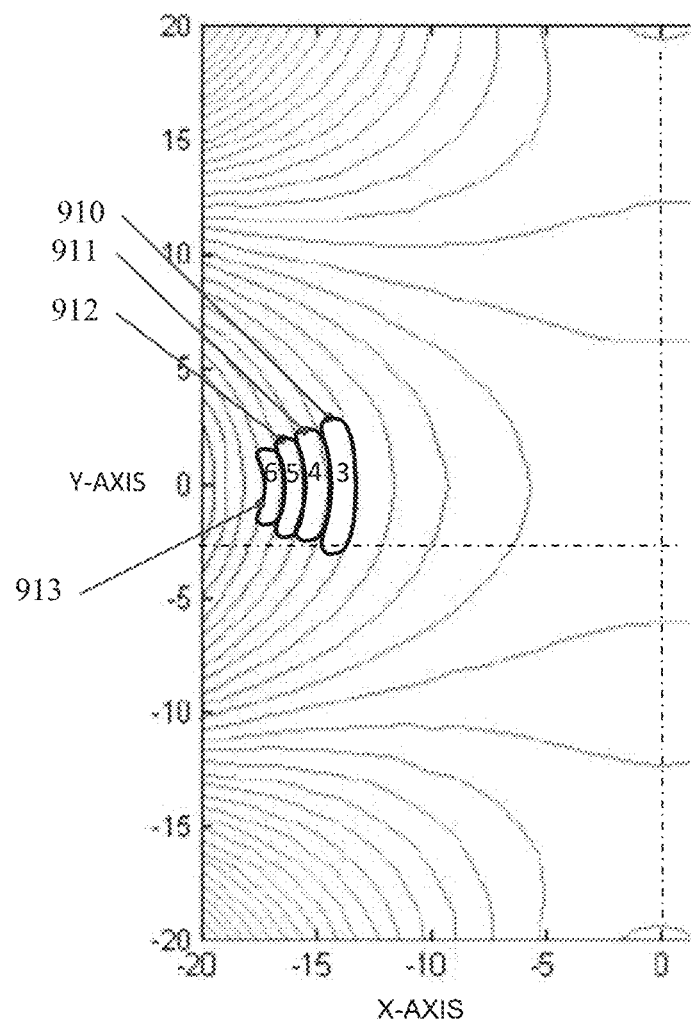
FIG. 9C is another sectional illustration of the "homogeneous" static magnetic field of the arrangement of FIG. 9A in the square shown in FIG. 9A. The field is perpendicular to an axis. Contours of equal static magnetic field amplitude are shown disposed adjacent each other in a direction toward one of the magnets.

FIG. 9C shows the contour at 910 in more detail, as well as similar contours 911, 912, 913 disposed adjacent each other in a direction toward one side of the magnets (904A and 904B in FIG. 9A). It is contemplated that a longitudinally extending RF antenna coil (118B in FIG. 3A) may be positioned and shaped along any or all of contours 910, 911, 912, 913, and a nonmagnetic, electrically non-conductive sample chamber (not shown), such as may be made from glass or TEFLON plastic may be disposed within such antenna coil or coils. NMR experiments may be performed within samples disposed within any one of, or any combination of the cross-sectional areas defined by the contours 910-913 by suitable selection of RF frequency and RF bandwidth to correspond to the cross sectional areas defined by any one or more of the contours 910-913. In this way, NMR signals may include both surface-effect related signals and signals from the bulk volume of a sample substantially unaffected by surface effects. It may be noted that sample chambers configured to fit within and to conform at their outer surface to two different contours may be described as having a boundary defined by substantially at most two values of static magnetic field amplitude, it being recognizable that the chamber boundary between the contours represents only a small portion of the total surface area of the sample chamber boundary. By analyzing detected NMR signals in the frequency domain, the position within any one or more of the contours 910-913 of the NMR signals may be determined, and surface relaxivity may be separately analyzed from bulk relaxivity of a sample placed within a suitable sample chamber. As explained above with reference to all the prior example embodiments, the longitudinal dimension of the magnets and the radio frequency antenna(s) may be selected such that the amplitude distribution and the polarization direction distribution of the static and radio frequency magnetic fields is substantially equal along the full longitudinal dimension of the sample chamber (not shown) such that at least part of a boundary thereof is along a surface of substantially equal static magnetic field amplitude. Thus, FIG. 9C represents only one cross section in a plane transverse to the longitudinal dimension wherein the static magnetic field amplitude and direction distribution is substantially constant.

Figure 10:
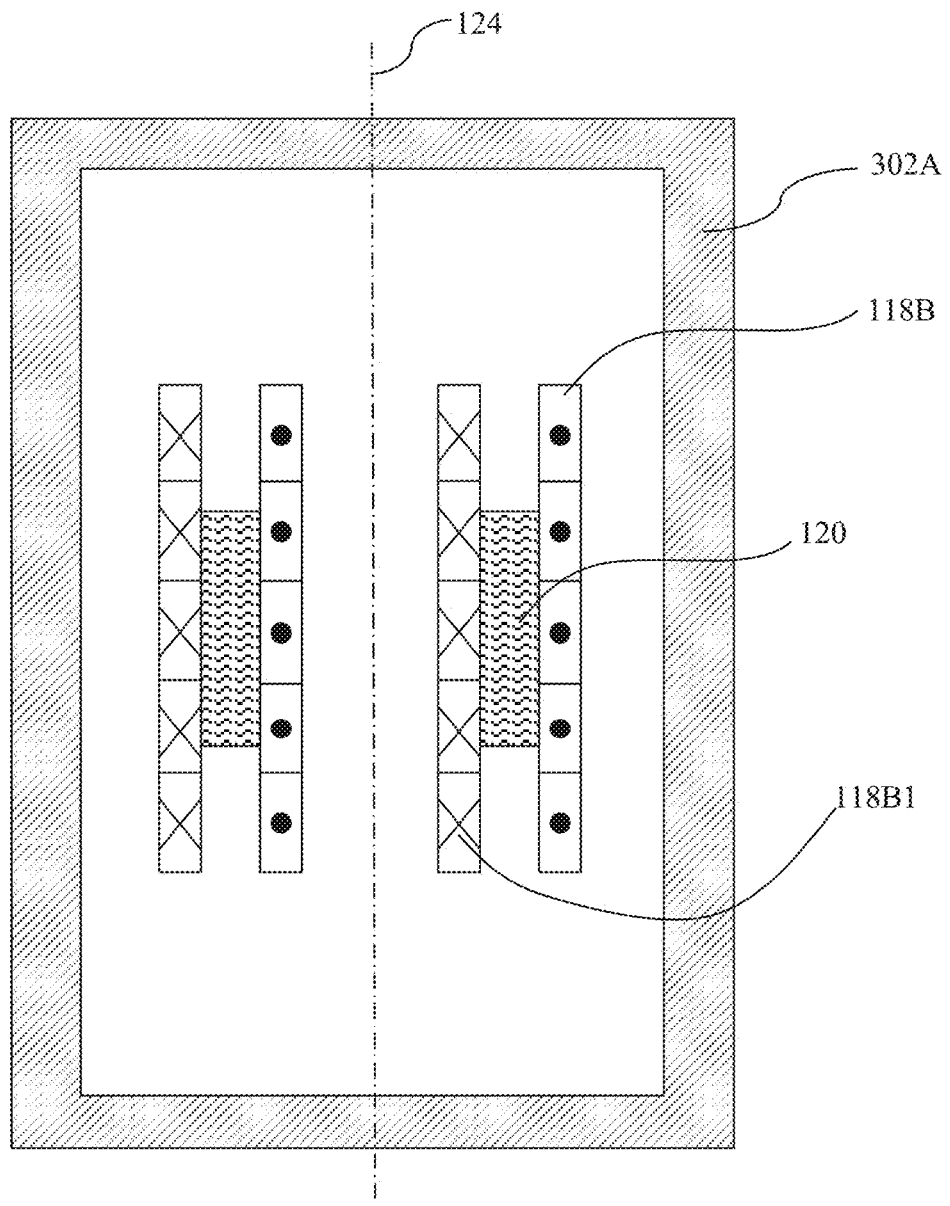
FIG. 10 shows an example RF shield.

FIG. 10 shows an example RF shield 302A made from electrically conductive material such as copper. An outer RF antenna coil 118B and an inner RF antenna coil 118B1 of slightly smaller diameter bound a sample volume 120. The coils 118B, 118B1 are wound in opposed directions so as to limit the extend of the RF magnetic field generated by the antenna coils 118B, 118B1 to being substantially within the sample volume. The example embodiment of FIG. 10 may use a magnet as explained with reference to FIGS. 2A and 2B, or external magnets as explained with reference to FIG. 5 or FIG. 9A, for example.

Figure 11:
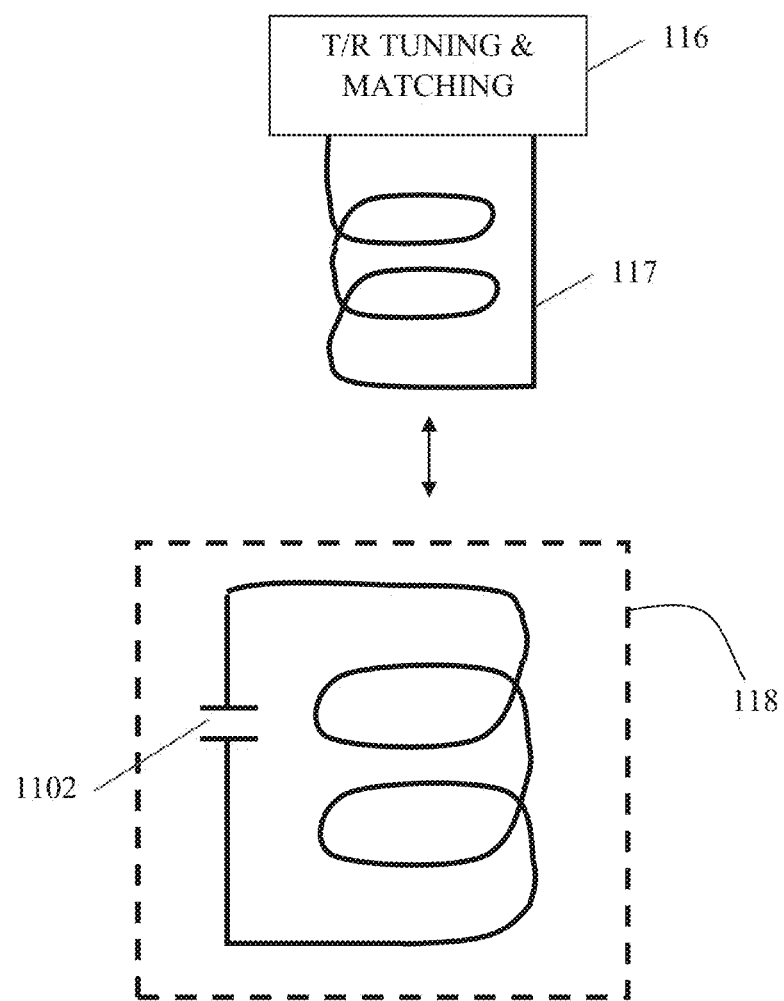
FIG. 11 shows an example of an inductively coupled sensor including a tuning capacitor connected to the RF coil.

As explained previously, it may be advantageous in some embodiments to have effectively "disposable" sensors (118 in FIG. 1) that are configured to hold very small (in the range of microliters) samples for analysis. The example electronic circuitry of FIG. 1 may be disposed in a separate instrument cabinet (not shown), and a sensor such as shown in FIG. 3A or FIG. 7 may be made in quantities to enable use thereof with only a single sample for NMR measurement and measurement analysis. FIG. 11 shows an example of an inductively coupled sensor 118 including a tuning capacitor 1102 connected to the RF coil 118B or coils (e.g., inner coil 118B1 in FIG. 3A). An inductive coupling 117 such as a coil type antenna may be coupled to the T/R tuning and matching circuit 116 so that placement of a "disposable" sensor 118 such as shown in FIG. 11 proximate the inductive coupling 117 may enable performing NMR measurements on the sample, and subsequent disposal of the sensor 118 after use with a single sample.

Figure 12:
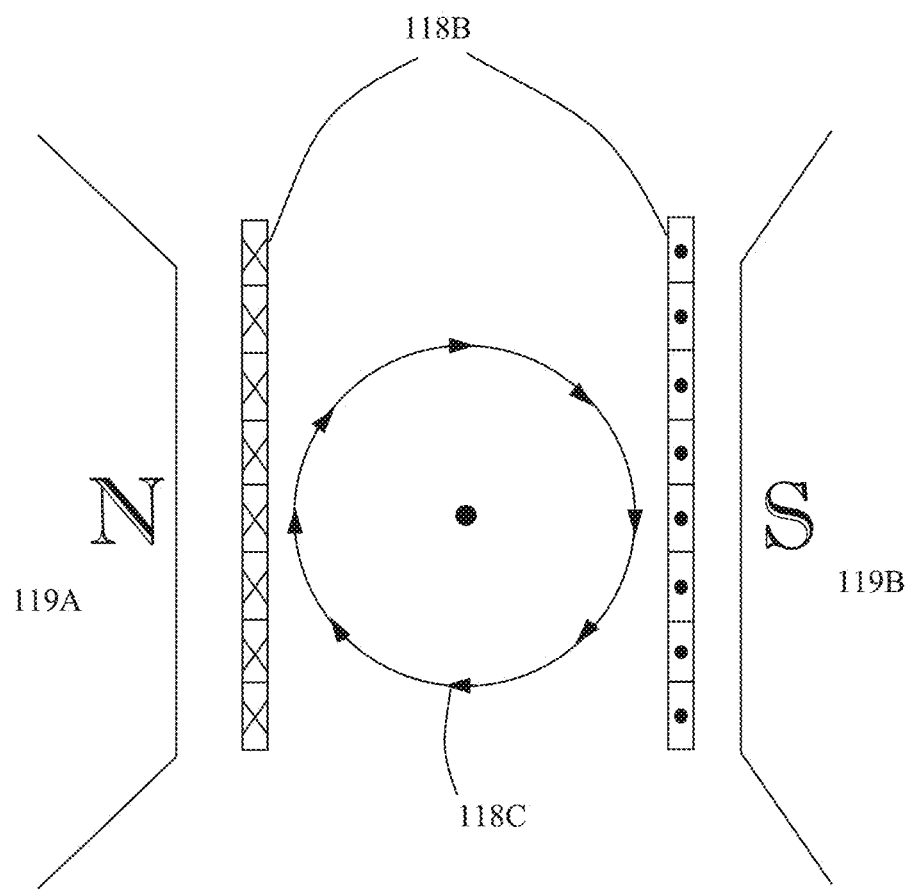
FIG. 12 shows example orthogonal RF coils in a cross-section perpendicular to the axis.

FIG. 12 shows example orthogonal RF coils in a cross-section perpendicular to an axis. An RF receiving antenna coil 118B may be wound as in the previously described embodiments. A separate, orthogonal dipole moment direction transmitter antenna coil 118C may be disposed in the static magnetic field. The transmitter antenna coil 118C may induce the required RF magnetic field in the sample to induce NMR phenomena in the sample, while the RF receiving antenna coil detects electromagnetic energy induced by the NMR phenomena and transmits the detected energy to the receiver (FIG. 1). A possible benefit of the example embodiment shown in FIG. 12 is that "ringing" of transmitter antenna 118C substantially does not induce any related signal in the receiving antenna 118B, thus reducing the "dead time" of the receiving antenna 118B. The embodiment of FIG. 12 may include a magnet structure including magnets 119A, 119B arranged such as shown in FIG. 6 or FIG. 9A. Both antennas 118B, 118C can operate at the same time and perform transmission and receiving of RF, but having a phase shift between them (typically 90 degrees). This may provide a signal-to-noise ratio (SNR) S/N improvement of a factor of $\sqrt{2}$.

Figure 13A:
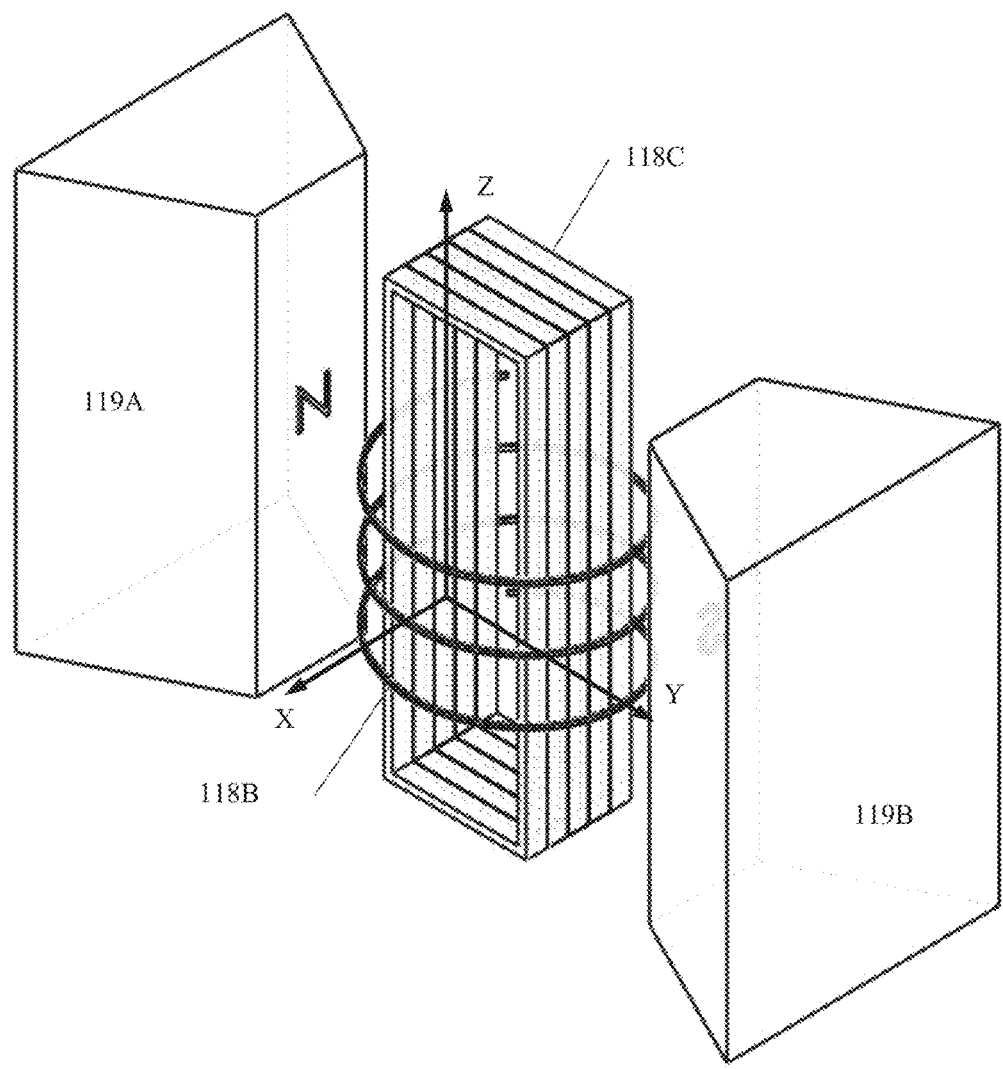
FIG. 13A shows a 3-dimensional sketch of the orthogonal RF coils of FIG. 12.

FIG. 13A shows a 3-dimensional sketch of the orthogonal RF antenna coils 118C, 118B of FIG. 12.

Figure 13B:
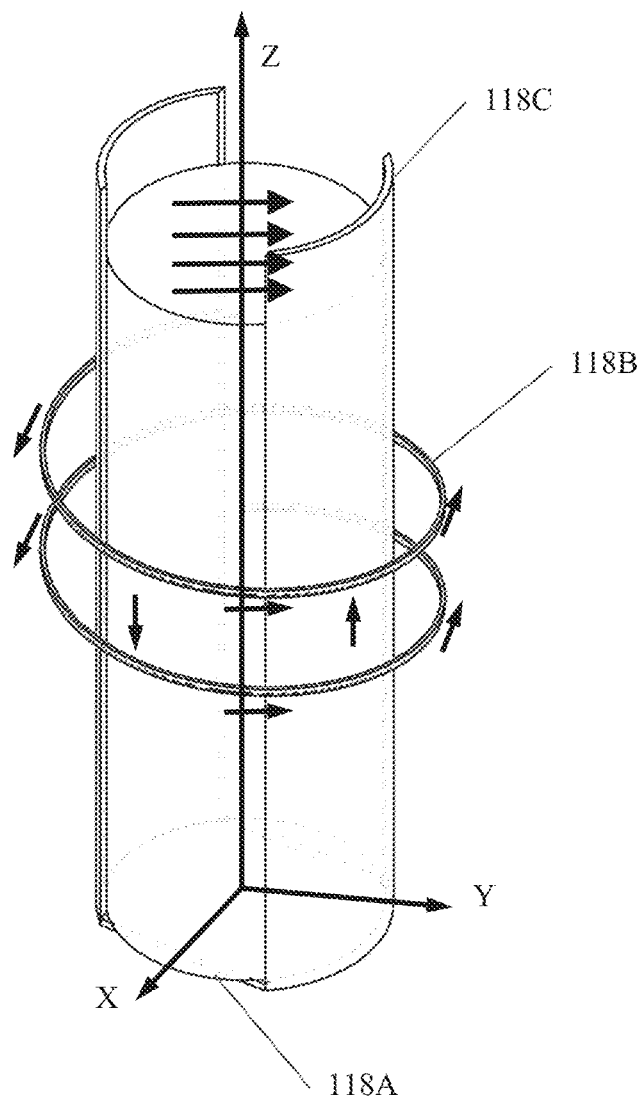
FIG. 13B shows a 3-dimensional sketch of orthogonal RF coils for a cylindrical magnet-antenna configuration of FIG. 2A and FIG. 2B.

FIG. 13B shows a 3-dimensional sketch of orthogonal RF coils 118B, 118C for a cylindrical magnet-antenna configuration such as the magnet arrangement shown in FIG. 2A and FIG. 3A. In the example embodiment of FIG. 13B, the transmitter antenna coil 118C may be a double sided solenoid coil having a dipole moment direction perpendicular to the loop direction of the coil and also perpendicular to the magnetization direction of the magnet 118A.

Figure 14A:
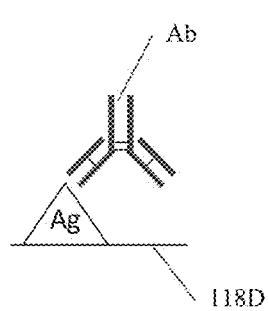
FIG. 14A shows a surface assay in which NMR surface relaxivity is altered primarily by an antibody being bound to an analyte antigen.

FIG. 14A shows a surface assay in which NMR surface relaxivity is altered primarily by an antibody Ab being bound to an analyte antigen Ag. To detect the presence of an antigen Ag by a surface assay, a surface 118D (for example, a surface of the sample chamber described with reference to FIGS. 3A, 4, 5, 6 and 7) is coated with a selected antigen Ag and the binding of an antigen-specific antibody Ab to the antigen-coated surface 118D is inhibited by test solutions containing a soluble primary antibody. During and after an incubation period (depending on the particular antigen and antibody) has elapsed, NMR measurements may be performed on a sample in the sample chamber. The degree and rate of change in relaxation times T1 and T2 and diffusion constant from NMR measurements made proximate to the surface 118D of the sample chamber may be determined. Changes in the foregoing parameters and rate of changes thereof may be compared to either or both a prior calibration set of NMR measurements of diffusion constant, T1 and T2 made proximate to the sample chamber surface 118D and to NMR measurements of T1, T2 and the diffusion constant in the bulk volume (see FIG. 9C) of the sample substantially free of surface related effects. A calibration set of measurements may be made, for example by coating the surface of the sample chamber with either the selected antigen Ag or the selected antibody Ab, and exposing the selected antigen Ag or antibody Ab to the relevant binding antibody Ab or antigen Ag. Thereafter, NMR surface relaxivity and diffusion constants may be measured. The surface relaxivity and diffusion constants thus measured reflect the values that will be measured if the specific antibody Ab is bound to the relevant antigen Ag coating the surface (or vice versa as shown in FIG. 14D) in any particular sample.

Figure 14B:
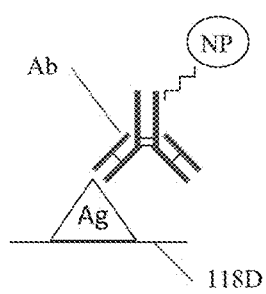
FIG. 14B shows a surface direct assay in which NMR surface relaxivity is altered primarily by an antibody conjugated to a nanoparticle being bound to an analyte antigen.

FIG. 14B shows a surface direct assay in which NMR surface relaxivity is altered primarily by an antibody Ab conjugated to a nanoparticle NP being bound to an analyte antigen Ag. To detect the presence of the antigen Ag by a surface direct assay, a surface 118D (e.g., of the test chamber as set forth above) is coated with a selected antigen Ag and the binding of a specific antibody-superparamagnetic nanoparticle Ab-NP conjugated to the antigen-coated surface is inhibited by test solutions containing a soluble primary antibody-nanoparticle. During and after a selected incubation period, the degree of changes in relaxation times T1 and T2 and diffusion constant proximate to the surface 118D are measured as explained above. The amount of change is compared to either or both a prior calibration measurement set made as explained with reference to FIG. 14A and to measurement in the bulk portion of the sample substantially free of surface effects as explained above. Note: Since the specific antibody-superparamagnetic nanoparticle Ab-NP conjugated will be magnetized in an applied static magnetic field, they may cluster at one surface by being magnetically attracted. Using two opposed cylindrical magnets as shown in FIG. 3B will reduce the external static magnetic field to zero.

Figure 14C:
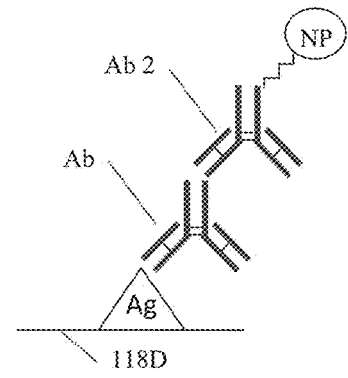
FIG. 14C shows a surface indirect assay in which NMR surface relaxivity is altered primarily by an antibody being bound to an analyte antigen followed by a secondary antibody conjugated to a nanoparticle being bound to the primary antibody.

FIG. 14C shows a surface indirect assay in which NMR surface relaxivity is altered primarily by an antibody Ab being bound to an analyte antigen Ag. The analyte antigen Ag is followed by a secondary antibody Ab2 conjugated to a nanoparticle NP being bound to the analyte antibody Ab. To detect the antigen Ag by a surface indirect assay, a surface 118D (e.g., in the test chamber as set forth above) is coated with a selected antigen Ag and the binding of a specific analyte antibody Ab conjugated to the antigen-coated surface is inhibited by test solutions containing the analyte antibody. Unbound analyte antibody Ab is washed out and an antigen-specific antibody Ab2 conjugated to a nanoparticle NP is added. During and after another incubation, NMR measurements may be made as explained above and the degree of change in relaxation times T1 and T2 and diffusion constant proximate the surface 118D may be determined explained above. The amount of change in the foregoing measurements with reference to prior calibration measurements and/or to measurement in the bulk of the sample volume as explained above may be determined to detect the presence of the analyte antibody Ab in the sample.

Figure 14D:
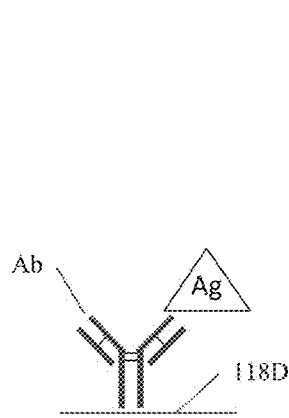
FIG. 14D shows a capture surface assay in which NMR surface relaxivity is altered by an analyte antigen being bound to a captured antibody.

FIG. 14D shows a capture surface assay in which NMR surface relaxivity is altered by an analyte antigen Ag being bound to a captured antibody Ab. To detect an antigen Ag by a capture surface assay, a surface 118D (e.g., of the sample chamber as explained above) is coated with a specific (capture) antibody Ab followed by incubation with test solutions containing a selected antigen Ag. After a selected incubation period, the degree of change in NMR relaxation times T1 and T2 and diffusion constant proximate the surface are determined as explained above by comparison to a prior calibration measurement set and/or to a measurement in the bulk part of the sample as explained above.

Figure 14E:
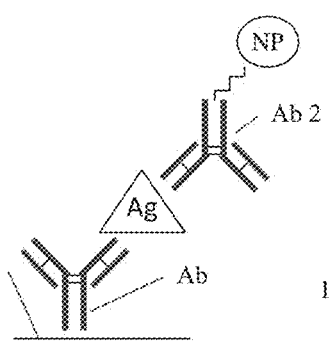
FIG. 14E shows a capture surface direct assay in which NMR surface relaxivity is altered by an analyte antigen being bound to a captured antibody followed by a primary antibody conjugated to a nanoparticle being bound to the analyte antigen.

FIG. 14E shows a capture surface direct assay in which NMR surface relaxivity is altered by an analyte antigen Ag being bound to a captured antibody Ab2 followed by a primary antibody Ab conjugated or not conjugated to a nanoparticle NP. The foregoing conjugation is bound to the analyte antigen Ag. To detect an antigen by a capture surface direct assay, a surface 118D is coated with a specific (capture) antibody Ab followed by a selected incubation period using a test solution containing an antigen Ag. Unbound antigen Ag is washed out and an antigen-specific antibody Ab conjugated or not conjugated to a nanoparticle NP is added, followed by another selected incubation period. During and after the second incubation period, the degree and rate of change in relaxation times T1 and T2 and diffusion constant proximate the surface are determined substantially as explained above with reference to FIG. 14A.

Figure 14F:
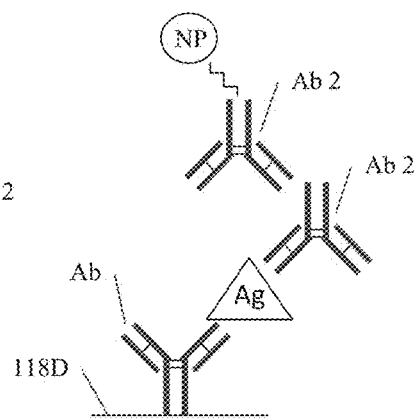
FIG. 14F shows a capture surface sandwich assay in which NMR surface relaxivity is altered by an analyte antigen being bound to a captured antibody followed by a primary antibody being bound to the analyte antigen, followed by a secondary antibody conjugated to a nanoparticle being bound to the primary antibody.

FIG. 14F shows a capture surface sandwich assay in which NMR surface relaxivity is altered by an analyte antigen being bound to a captured antibody followed by a primary antibody being bound to the analyte antigen, followed by a secondary antibody conjugated or not conjugated to a nanoparticle being bound to the primary antibody. To detect an antigen by a capture surface sandwich assay, a surface 118D is coated with a specific (capture) antibody Ab followed by a selected incubation period using test solutions containing an antigen Ag. Unbound antigen is washed out and an antigen-specific antibody Ab2 conjugated or not conjugated to a nanoparticle NP is added, followed by another incubation. During and after the second incubation period, the degree and rate of change in relaxation times T1 and T2 and diffusion constant in a surface layer are determined substantially as explained above with reference to FIG. 14A.

In all of FIGS. 14A through 14F, the surface 118D (inner or outer) of the sample chamber (whether made from glass, TEFLON plastic, copper shield or other material) may define the surface on which the above described coating is performed and the described phenomena take place.

Figure 15:
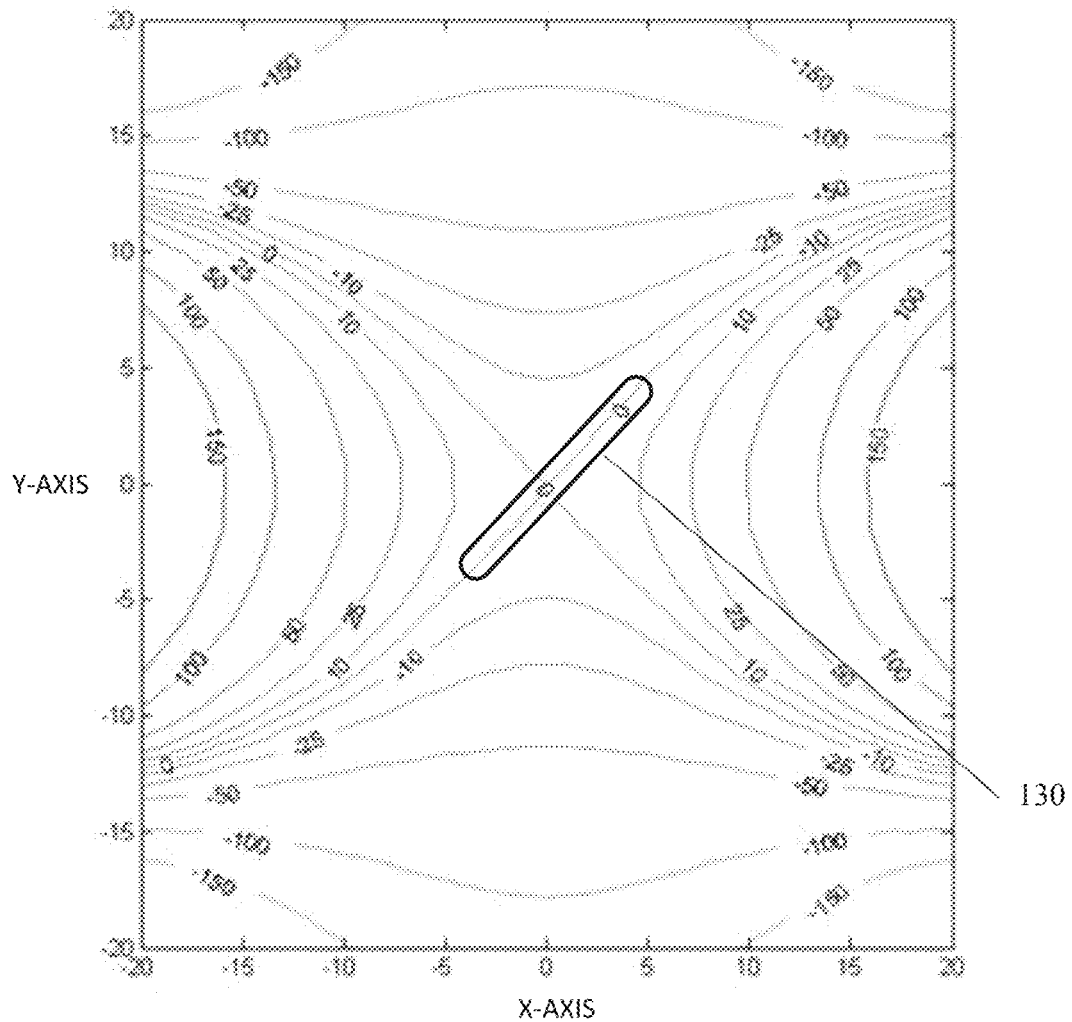
FIG. 15 is a sectional illustration of an example "homogeneous" static magnetic field using a magnet arrangement as in FIG. 9A having a thin volume along a line of equal static magnetic field strength. The field is perpendicular to an axis. Contours of equal static magnetic field amplitude are shown.

FIG. 15 is a sectional illustration of an example "homogeneous" magnetic field using a magnet arrangement as in FIG. 9A having a thin volume along a line 130 of equal static magnetic field strength. The field is perpendicular to an axis. Contours of equal static magnetic field magnitude are shown.

Figure 16A:
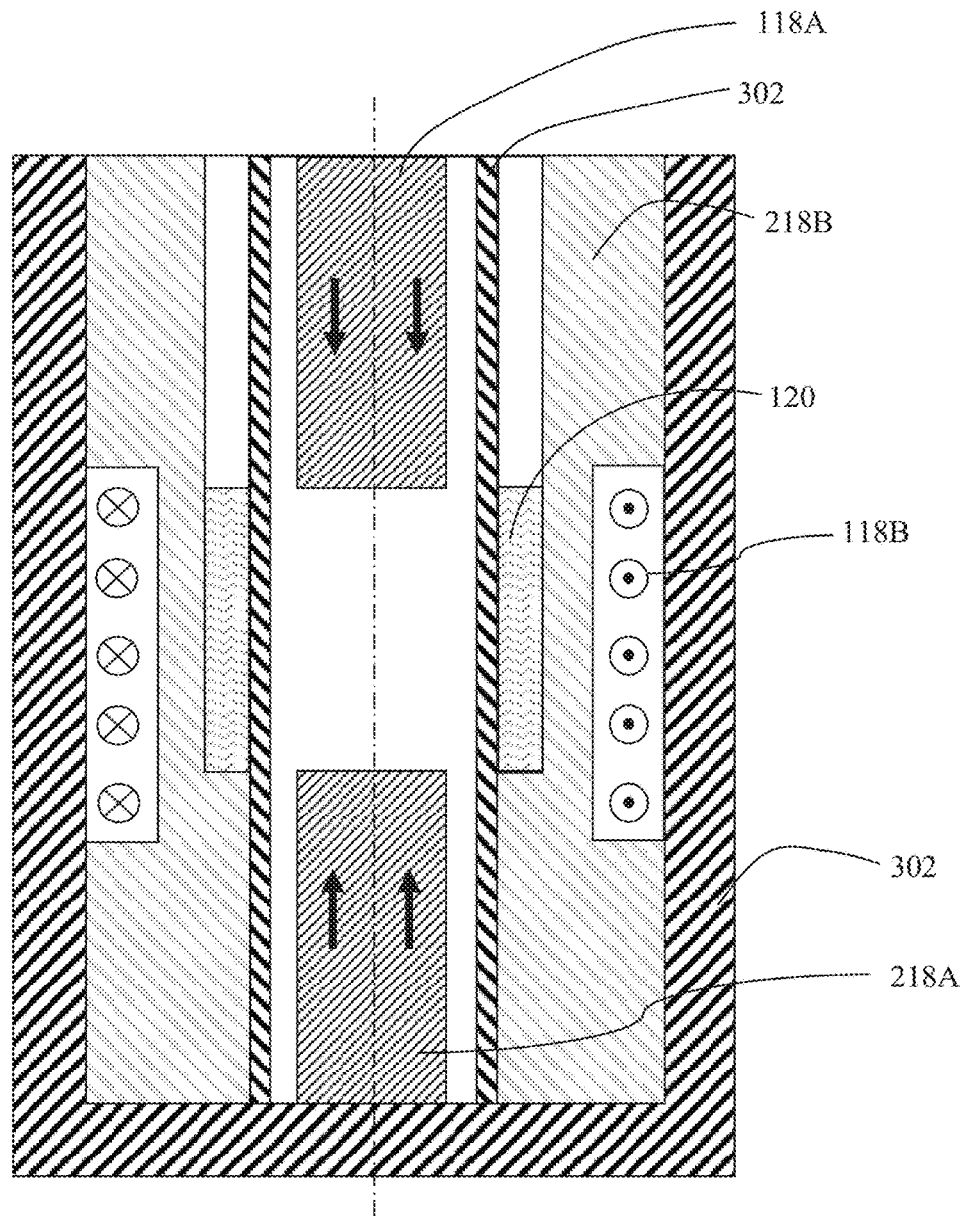
FIG. 16A is a detailed sectional illustration of another sensor in a plane parallel to an axis and illustrates example arrangements of the magnet, RF coil, magnetization direction and the current direction with reference to the sample being analyzed in a substantially homogeneous radial static magnetic field.
Figure 16B:
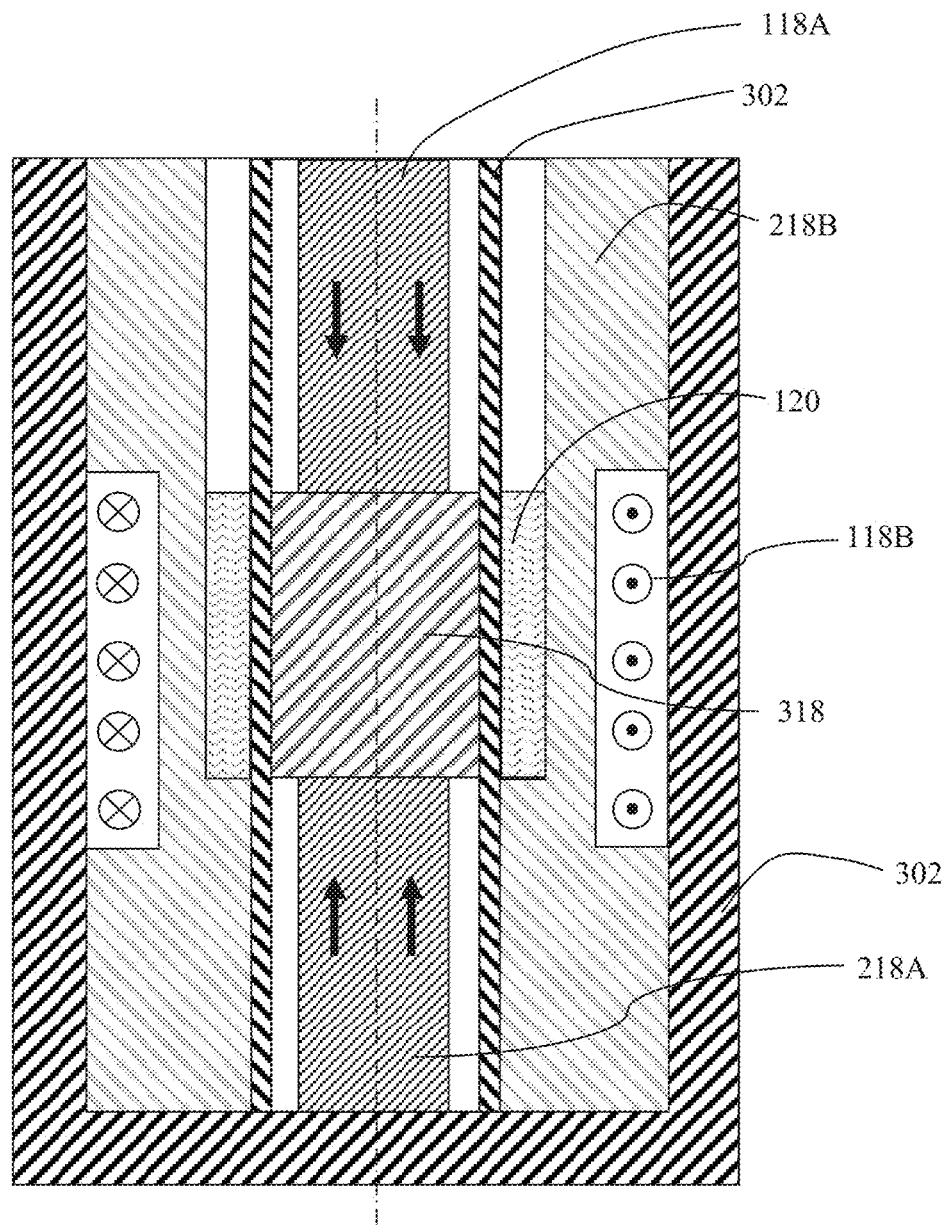
FIG. 16B is a detailed sectional illustration of another sensor in a plane parallel to an axis and illustrates example arrangements of the magnet, RF coil, magnetization direction and the current direction with reference to the sample being analyzed in a substantially radial static magnetic field.

FIG. 16A is a detailed sectional illustration of another embodiment of a NMR sensor in a plane parallel to a longitudinal axis. FIG. 16A illustrates another possible example arrangements of a magnet in the form of two, longitudinally polarized, opposed polarity magnets 118A, 218A. An RF antenna, which may be a solenoid coil 118B may be disposed as shown approximately in the longitudinal center of the space between the magnets 118A, 218A. Magnetization direction and the current direction are indicated with reference to the sample being analyzed, shown at 120. The sample 120 is disposed in a substantially homogeneous radial static magnetic field. A radio frequency shield 302 may be arranged as shown to limit the extent of the RF magnetic field such that the filling factor of the sample 120 will provide adequate SNR. FIG. 16B is a detailed sectional illustration of another embodiment of a NMR sensor in a plane parallel to a longitudinal axis. FIG. 16A illustrates another possible example arrangements of a magnet in the form of two, longitudinally polarized, opposed polarity magnets 118A, 218A. A magnetic pole piece 318 may be disposed between the magnets 118A, 218A. An RF antenna, which may be a solenoid coil 118B may be disposed as shown approximately in the longitudinal center of the space between the magnets 118A, 218A. Magnetization direction and the current direction are indicated with reference to the sample being analyzed, shown at 120. The sample 120 is disposed in a substantially a substantially radial static magnetic field. A radio frequency shield 302 may be arranged as shown to limit the extent of the RF magnetic field such that the filling factor of the sample 120 will provide adequate SNR.

Figure 17:
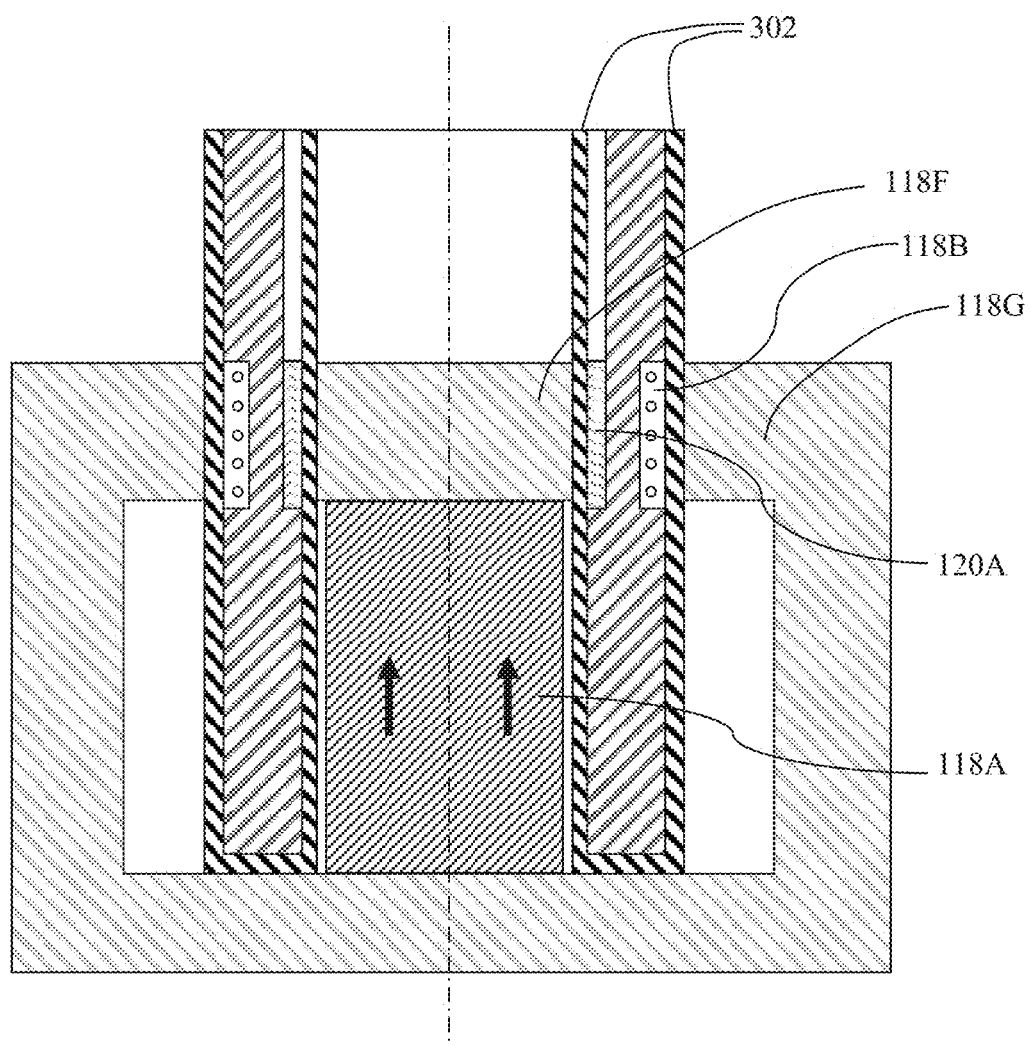
FIG. 17 is a detailed sectional illustration of yet another sensor in a plane parallel to an axis and illustrates example arrangements of the magnet, RF coil, magnetization direction and the current direction with reference to the sample being analyzed in a substantially radial static magnetic field.

FIG. 17 is a detailed sectional illustration of yet another embodiment of a sensor in a plane parallel to a longitudinal axis and illustrates an example arrangements of the magnet 118A, RF antenna coil 118B, magnetization direction and the RF current direction with reference to the sample 120 being analyzed. The sample 120 in the embodiment of FIG. 17 is disposed in a substantially radial static magnetic field. The magnet 118A may include an outer flux closure 118G disposed externally to the sample 120 and an inner flux closure 118F disposed inside the sample 120 and RF antenna 118B. The example embodiment in FIG. 17 may include an RF shield 302 as in the previously described embodiments to increase the filling factor for improved SNR.

In all of the foregoing example embodiments, two principal objectives of the configuration of the RF antenna coil(s) and/or shielding and the associated sample chamber may be: (i) the surface to volume ratio may be substantially enhanced by limiting the enclosed volume of the sample chamber with narrow limits on the radial spacing between the inner and outer sides of the sample chamber and associated RF magnetic field; and (ii) having a high sample "filling factor", which may be as high as unity (1.0) whereby substantially the entire sample chamber is within the area bounded by the RF magnetic field, thus enhancing the signal to noise ratio. In any of the foregoing example embodiments, measurement of near surface and surface-related NMR signals may be facilitated by having the RF antenna coil(s), RF shielding if used and the associated sample volume cross section be bounded along contours of equal static magnetic field amplitude, whatever the static magnetic field amplitude distribution is. By so arranging the shape of the RF magnetic field and corresponding sample chamber, it may be easier to make NMR measurements of surface-related NMR properties of the sample distinguishable from the bulk sample volume NMR properties of the sample (or to exclude the near surface and/or surface related NMR signals and associated properties from the bulk sample NMR signals and associated properties. The surface effects measured using any of the foregoing embodiments of an apparatus include at least one of spin-spin relaxation, spin-lattice relaxation, diffusion constant, and maximum NMR signal amplitude surface effects.

Embodiments of a sample chamber, magnet and RF antenna coil(s) and/or RF shield according to the various aspects of the present disclosure may enable measurements of NMR signals from within a small number of molecular thicknesses from the surface defined by the boundaries of the sample chamber by suitable selection of static magnetic field gradient and associated RF magnetic field frequency, or, selecting an RF magnetic field bandwidth and receiver bandwidth so that the total NMR signal detected is from the entire volume of the sample chamber, while surface and near surface NMR measurements may be made by selectively determining the signal content at RF frequencies within the received signal bandwidth that are associated with excitation of NMR phenomena at the static magnetic field amplitude and corresponding RF magnetic field frequency at positions proximate the surface(s) of the sample chamber. In some embodiments, by selecting a sample chamber to have a high surface to volume ratio, wherein surface affected NMR signals comprise a selected fraction of the total NMR signal, e.g., 25 to 50 percent, it may be possible to measure changes in surface relaxivity and diffusion constant substantially directly without the need to further analyze the NMR measurements with respect to position within the sample chamber.

Measurement of NMR signals from the entire sample chamber volume and from the near surface, irrespective of the sample chamber configuration and the measurement position within the sample volume may be made using well known RF pulsing sequences such as the CPMG (Carr-Purcell-Meiboom-Gill) sequence to determine relaxation times and diffusion coefficients of the materials being analyzed.

NMR methods for measuring presence of certain substances in a very small liquid sample may be based on simultaneously and optimally sensing T2 and T1 as described in U.S. Pat. Nos. 7,366,559, 7,355,360 and 7,355,402 issued to Taicher et al.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A nuclear magnetic resonance (NMR) apparatus, comprising:
   at least one magnet arranged to induce a static magnetic field in a sample chamber, the static magnetic field having a known amplitude distribution;
   at least one radio frequency antenna configured to induce a radio frequency magnetic field in the sample chamber at a predetermined frequency and a predetermined bandwidth; and
   wherein a boundary of the sample chamber is shaped such that a static magnetic field amplitude at the sample chamber boundary has substantially only a maximum and a minimum value, and wherein a first surface of the sample chamber is shaped to conform to a surface defined by the maximum value and a second surface of the sample chamber conforms to a surface defined by the minimum value.

2. The NMR apparatus of claim 1 wherein a boundary of the least one radio frequency antenna conforms to the sample chamber boundary.

3. The NMR apparatus of claim 1 wherein the at most two values are substantially equal.

4. The NMR apparatus of claim 1 wherein the predetermined frequency corresponding to one of the at most two values of the static magnetic field amplitude and the predetermined bandwidth are selected to excite NMR phenomena substantially exclusively proximate to the sample chamber boundary.

5. The NMR apparatus of claim 1 wherein a material sample is located inside the sample chamber wherein a ratio of a surface of the material sample to sample chamber interface with respect to a volume of the material sample is selected such that NMR phenomena induced in the sample depend substantially entirely on material sample to sample chamber interface effects.

6. The NMR apparatus of claim 5 wherein the material sample to sample chamber interface effects include at least one of spin-spin relaxation, spin-lattice relaxation, diffusion constant, and maximum NMR signal amplitude changes or rate of changes.

7. The NMR apparatus of claim 1 wherein the at least one magnet comprises a substantially cylindrical magnet polarized transversely to a longitudinal axis thereof disposed internally to the sample chamber and wherein the at least one first radio frequency antenna comprises a solenoid coil disposed at a selected radial distance from an exterior surface of the at least one magnet.

8. The NMR apparatus of claim 7 further comprising a second substantially cylindrical magnet disposed in a coaxially located opening in the at least one magnet, the second magnet polarized transversely to its longitudinal axis and rotatable within the opening such that an amplitude of the static magnetic field is selectively variable.

9. The NMR apparatus of claim 8 wherein a cross-section of the second magnet and the at least one magnet and a respective magnetization of the at least one magnet and the second magnet are selected such that a substantially zero static magnetic field amplitude is generated when polarization directions of the at least one and the second magnets are respectively opposed.

10. The NMR apparatus of claim 1 further comprising at least one magnet having two opposed poles disposed externally to the sample chamber, the at least two poles directed toward each other.

11. The NMR apparatus of claim 2 further comprising a radio frequency magnetic field shield shaped to conform to another boundary of the sample chamber.

12. The NMR apparatus of claim 11 wherein the radio frequency magnetic field shield comprises at least one of an electrically conductive, non-magnetic material and an additional radio frequency antenna having a same current density, connected in series with and in opposed polarity to the at least one radio frequency antenna.

13. The NMR apparatus of claim 12 wherein a shape of the radio frequency antenna and the radio frequency magnetic field shield are selected such that a NMR transmitting-receiving filling factor of the NMR apparatus is substantially equal to unity.

14. A method for making nuclear magnetic resonance (NMR) measurements, comprising:
   inducing a static magnetic in a region containing material to be analyzed, the static magnetic field having a static magnetic field direction perpendicular to a longitudinal axis, wherein a first surface of the region in a sample chamber is shaped to conform to a surface defined by the maximum value and a second surface of the region conforms to a surface defined by the minimum value of a static magnetic field amplitude;
   generating a radio frequency magnetic field of substantially uniform and azimuthally symmetric amplitude in the region for exciting nuclei of the material to be analyzed and having a radio frequency magnetic field direction substantially parallel to the longitudinal axis and perpendicular to the static magnetic field direction;
   detecting nuclear magnetic resonance signals from the material to be analyzed; and in a computer determining relaxation times and diffusion coefficients of the material to be analyzed, using the detected nuclear magnetic resonance signals whereby surface relaxivity is separately analyzable from bulk relaxivity of a sample placed within the sample chamber.

15. The method of claim 14 wherein the generating a radio frequency magnetic field includes generating a radio frequency magnetic field substantially exclusively within an annular cylinder radially located outside a permanent magnet and inside a solenoid antenna.

* * * * *